United States Patent
Franco et al.

(10) Patent No.: US 12,390,245 B2
(45) Date of Patent: Aug. 19, 2025

(54) SYSTEMS AND METHODS FOR A HAIR TRANSPLANT SYSTEM WITH EXTRACTION AND IMPLANTATION NEEDLES

(71) Applicant: THE GENERAL HOSPITAL CORPORATION, Boston, MA (US)

(72) Inventors: Walfre Franco, Westborough, MA (US); Esmeralda Ibarra-Silva, Boston, MA (US); William A. Farinelli, Boston, MA (US); Joshua Tam, Boston, MA (US); Richard Rox Anderson, Boston, MA (US); Lynn Drake, Boston, MA (US); Sandeep Korupolu, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 232 days.

(21) Appl. No.: 17/800,925

(22) PCT Filed: Feb. 22, 2021

(86) PCT No.: PCT/US2021/019115
§ 371 (c)(1),
(2) Date: Aug. 19, 2022

(87) PCT Pub. No.: WO2021/168448
PCT Pub. Date: Aug. 26, 2021

(65) Prior Publication Data
US 2023/0082466 A1 Mar. 16, 2023

Related U.S. Application Data

(60) Provisional application No. 62/979,504, filed on Feb. 21, 2020.

(51) Int. Cl.
*A61B 17/3205* (2006.01)
*A61F 2/10* (2006.01)
*A61B 17/00* (2006.01)

(52) U.S. Cl.
CPC .......... *A61B 17/32053* (2013.01); *A61F 2/10* (2013.01); *A61B 2017/00752* (2013.01)

(58) Field of Classification Search
CPC .... A61B 17/32053; A61B 2017/00752; A61B 2017/320064; A61B 2017/00969; A61B 2017/00367; A61F 2/10
See application file for complete search history.

(56) References Cited

U.S. PATENT DOCUMENTS 6,094,594 A * 7/2000 Tapper .................. A61N 1/325
604/20
2003/0097144 A1 5/2003 Lee
(Continued)

FOREIGN PATENT DOCUMENTS

WO 2019014677 A1 1/2019

OTHER PUBLICATIONS

International Search Report and Written Opinion issued in corresponding PCT Application No. PCT/US2021/019115, mailed May 20, 2021.
(Continued)

*Primary Examiner* — Tuan V Nguyen
(74) *Attorney, Agent, or Firm* — QUARLES & BRADY LLP

(57) ABSTRACT

Systems and methods are provided for performing a hair transplant using a hair transplant device. The hair transplant device comprises an extraction unit including a coring needle configured to extract at least one hair follicle from a donor site, an implanting unit removably coupled to the extraction unit, the implanting unit including a splitting
(Continued)

needle configured to create an opening in a recipient site, a housing coupled to the extraction unit, and a user interface extending from the housing and moveable relative to the housing. The user interface includes a pin movable within the coring needle relative to the housing.

29 Claims, 27 Drawing Sheets

(56) References Cited

U.S. PATENT DOCUMENTS

| | | |
|---|---|---|
| 2005/0096687 A1 | 5/2005 | Rassman et al. |
| 2007/0106307 A1 | 5/2007 | Bodduluri et al. |
| 2008/0234697 A1* | 9/2008 | DuBois ................ A61B 17/322 |
| | | 606/187 |
| 2009/0088720 A1* | 4/2009 | Oostman, Jr. ............. A61F 2/10 |
| | | 606/130 |
| 2010/0030234 A1 | 2/2010 | Bodduluri et al. |
| 2013/0226214 A1 | 8/2013 | Okuda |
| 2015/0305767 A1 | 10/2015 | Cole |
| 2021/0145476 A1 | 5/2021 | Franco et al. |

OTHER PUBLICATIONS

European Patent Office, Extended Search Report, Application No. 21757051.4, Feb. 20, 2024, 8 pages.

* cited by examiner

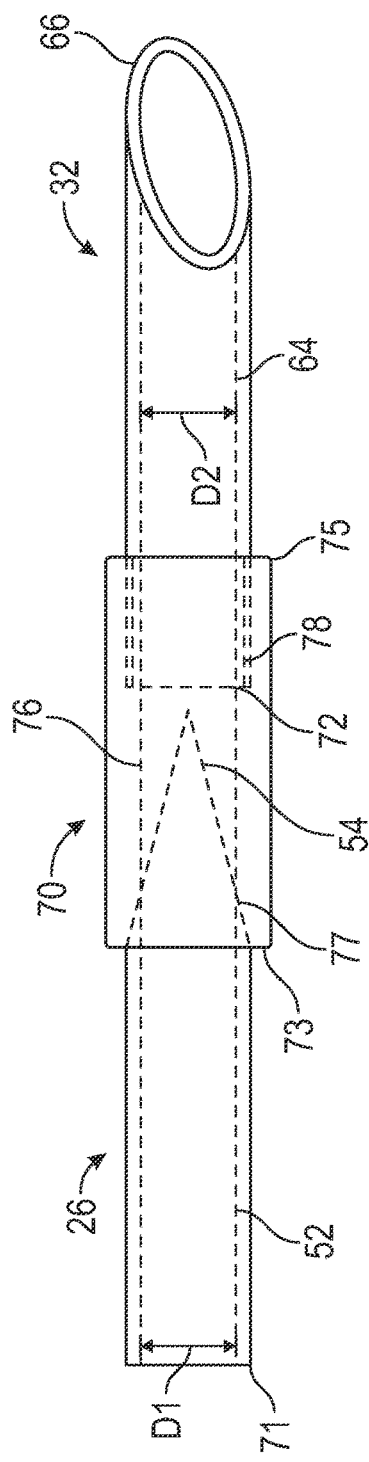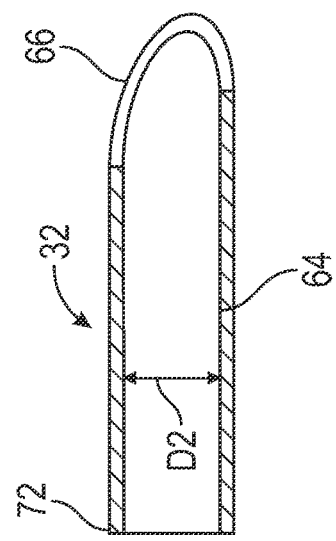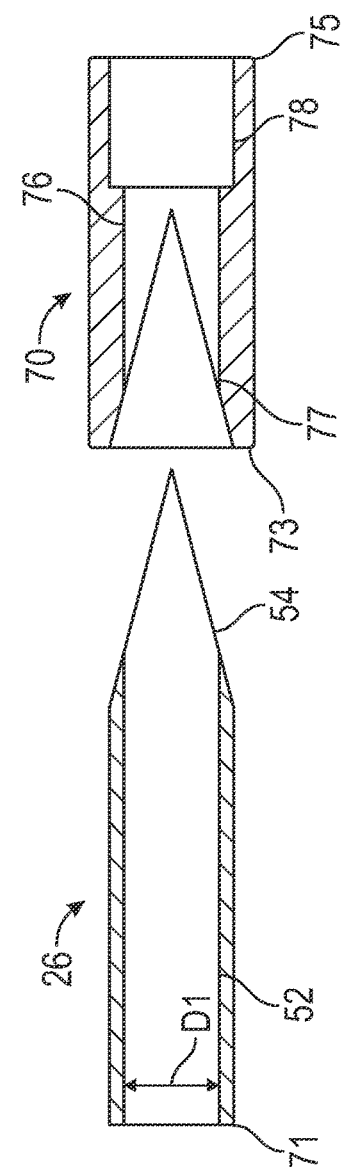
FIG. 7
FIG. 8

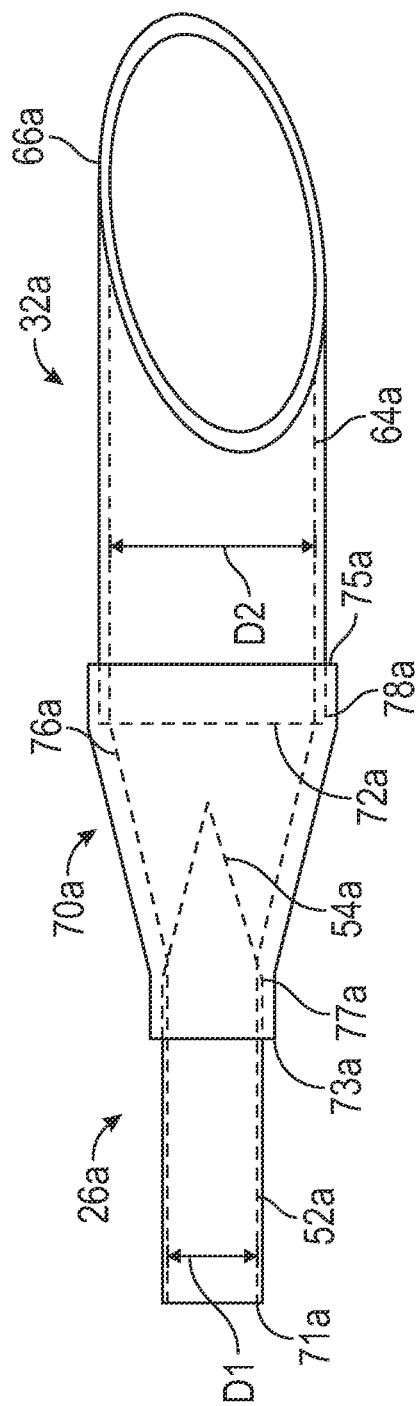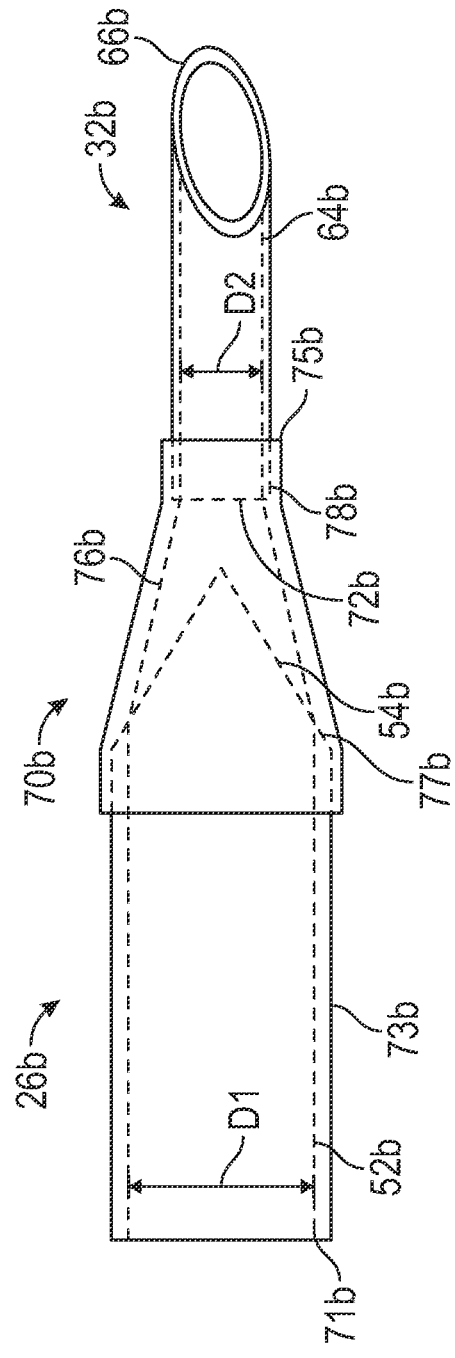

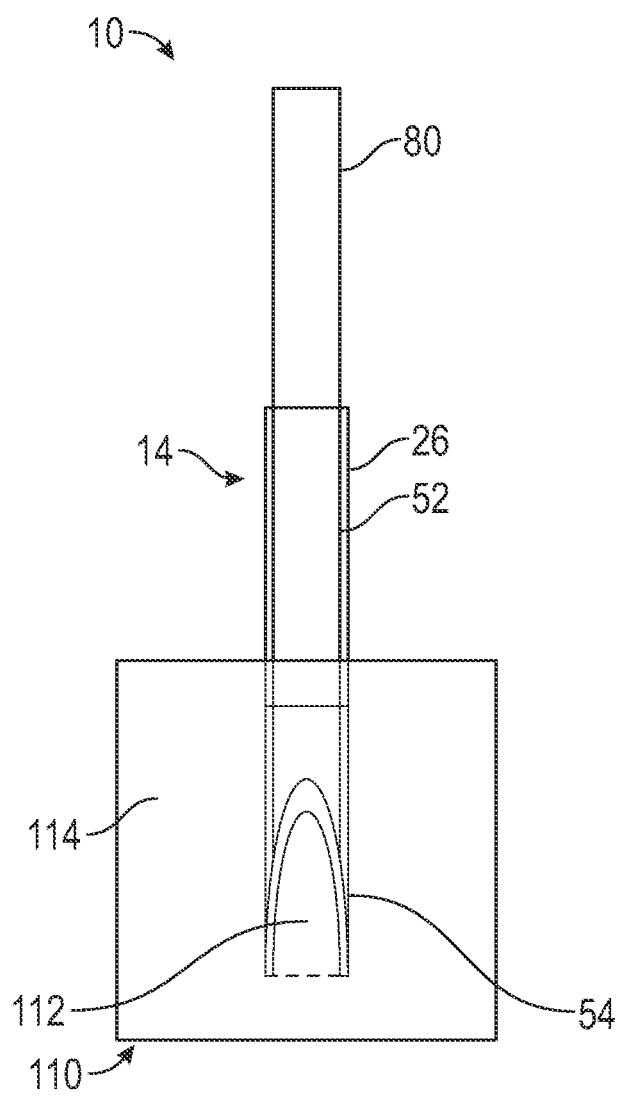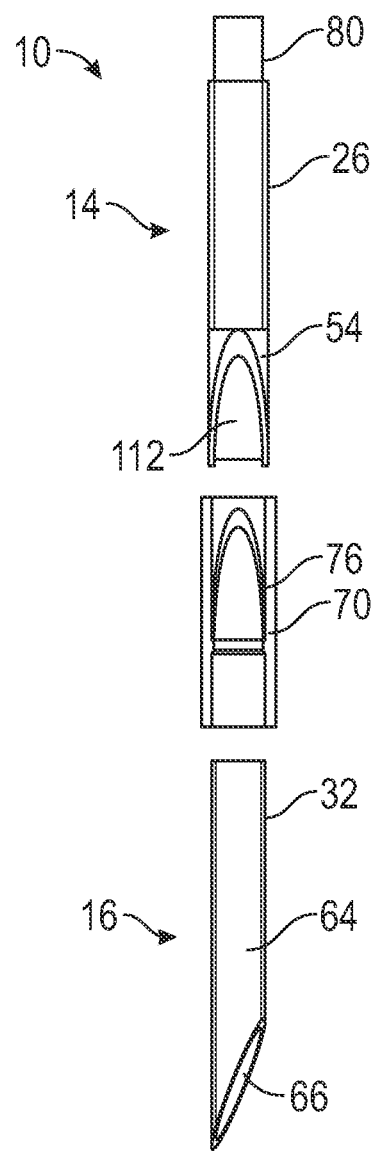
FIG. 12
FIG. 13

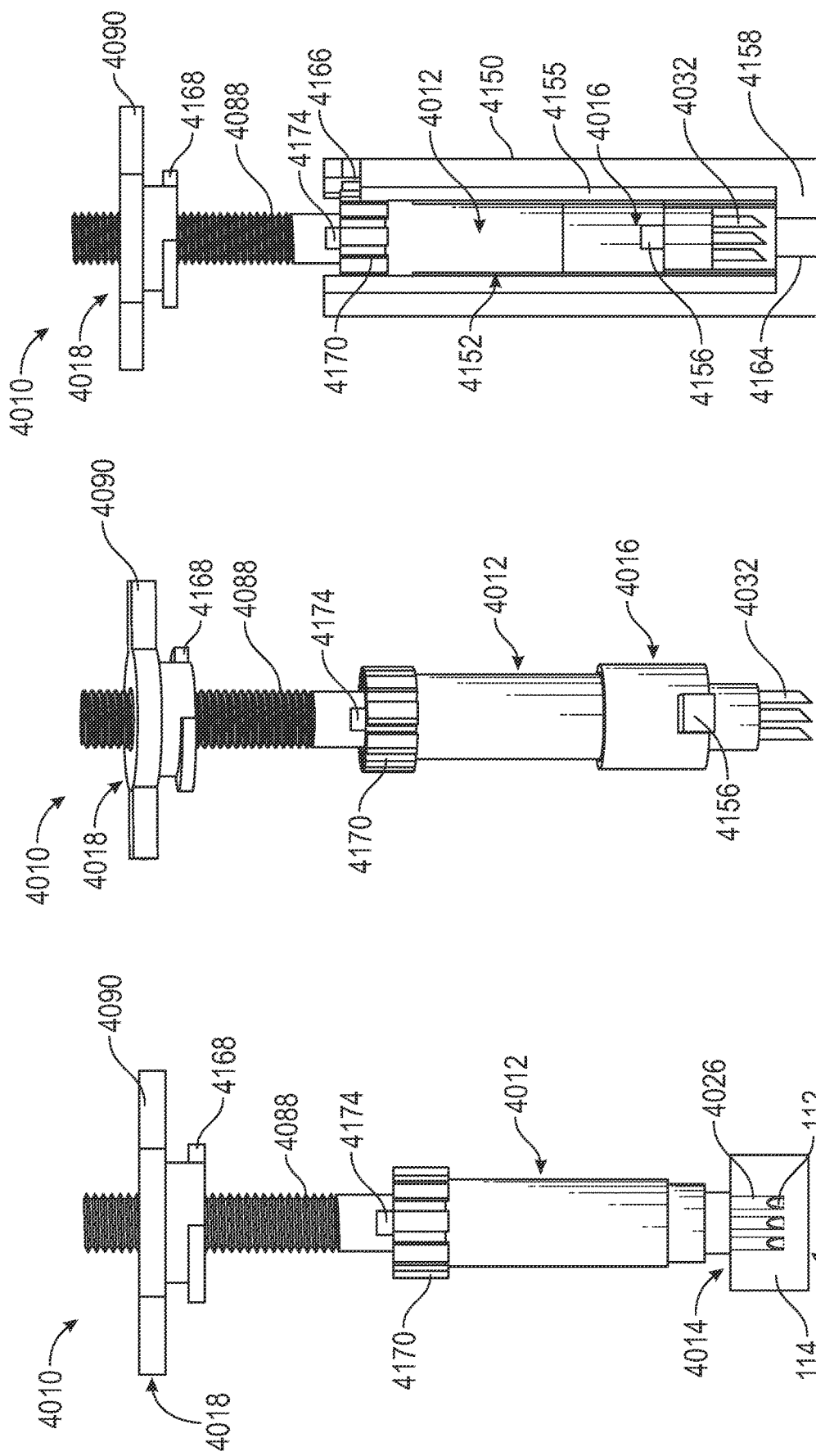

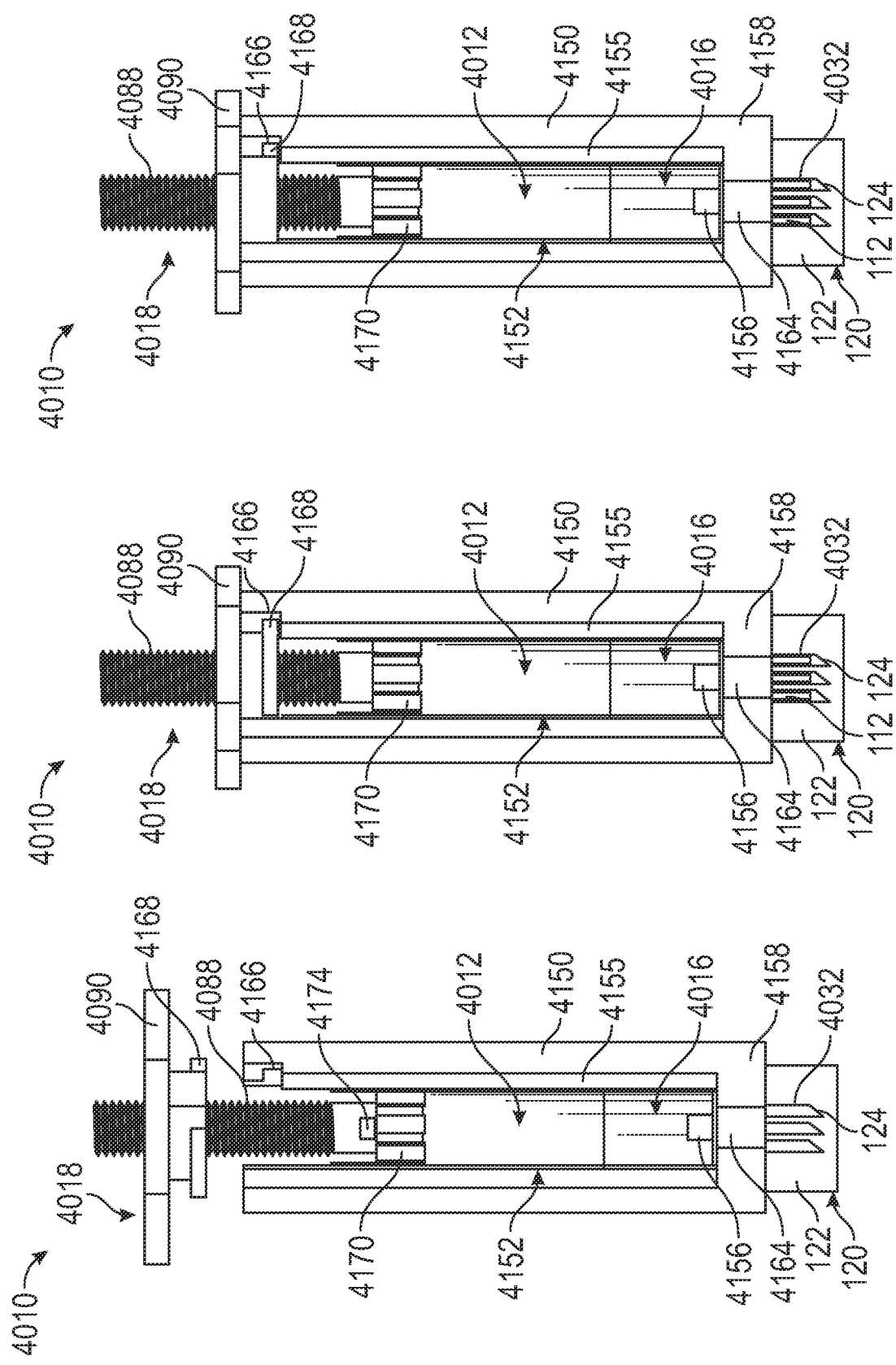

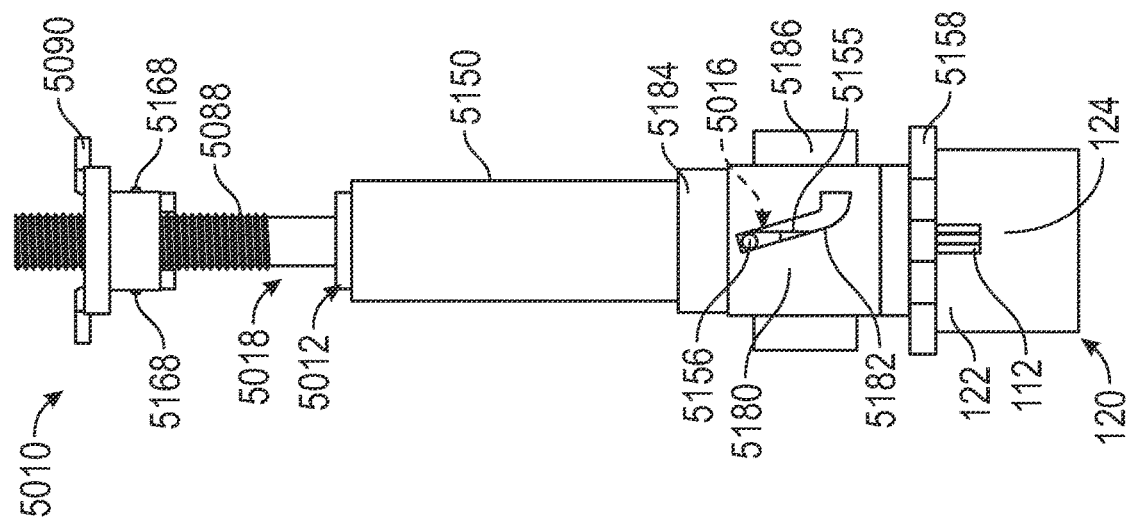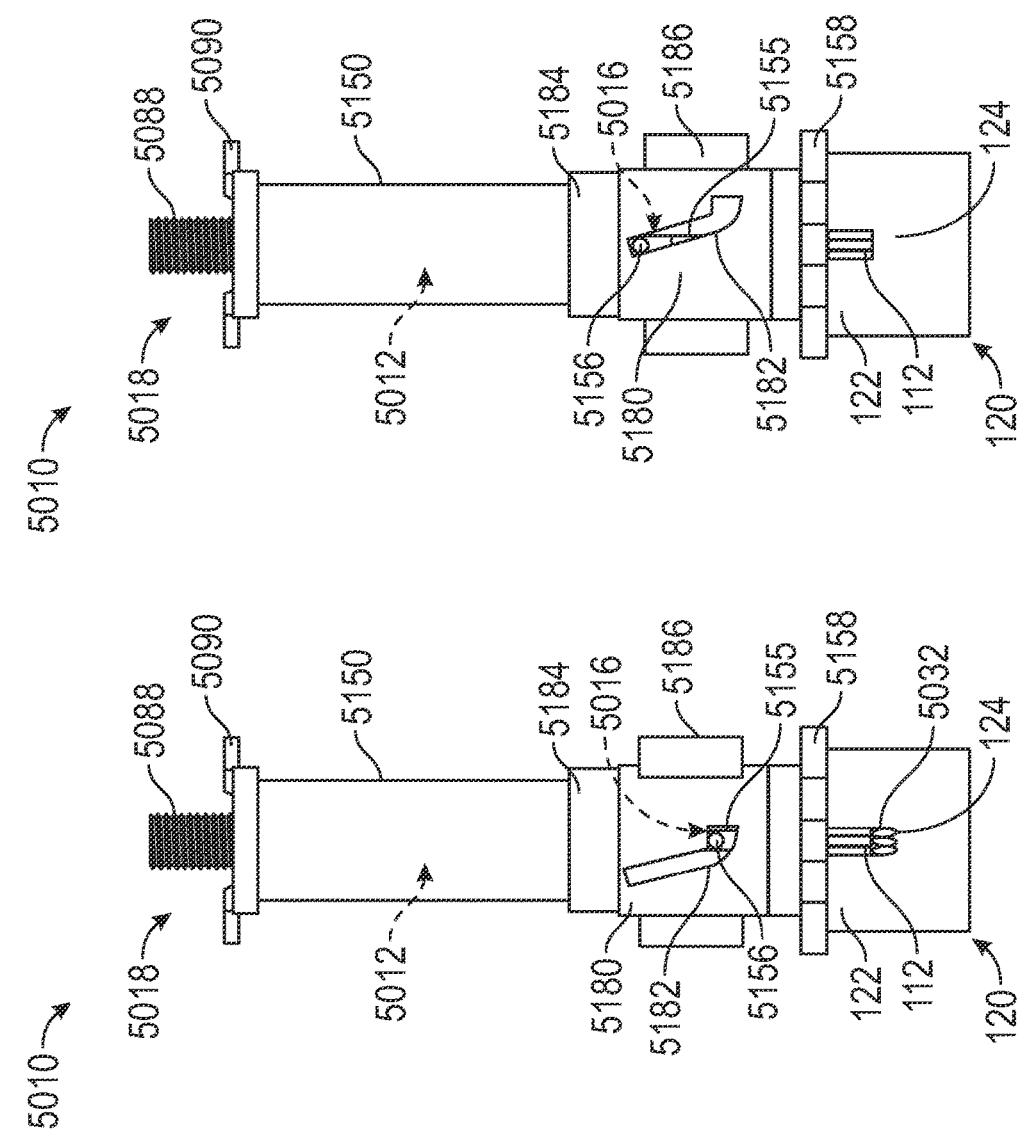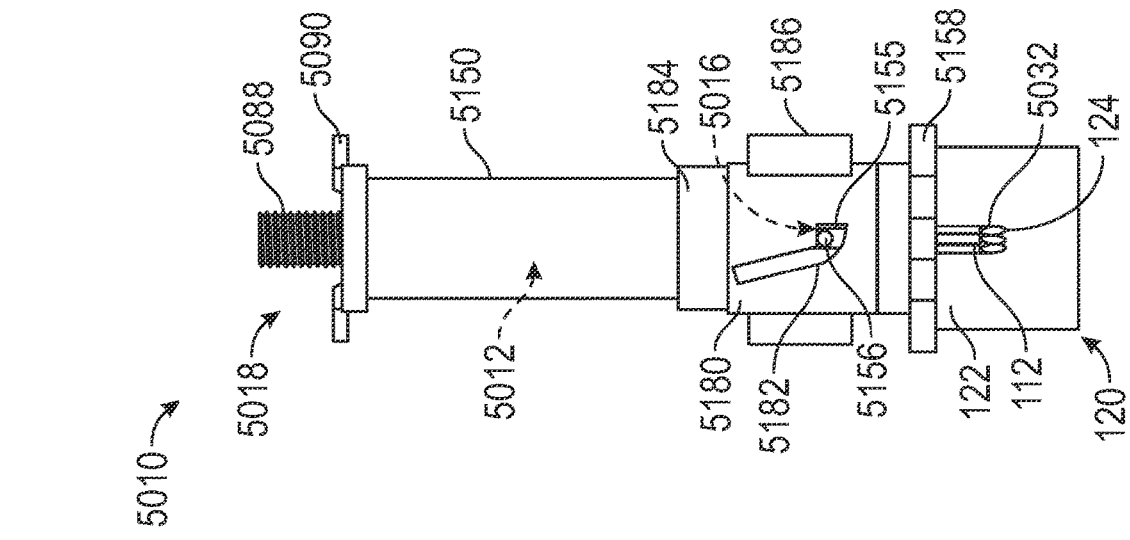

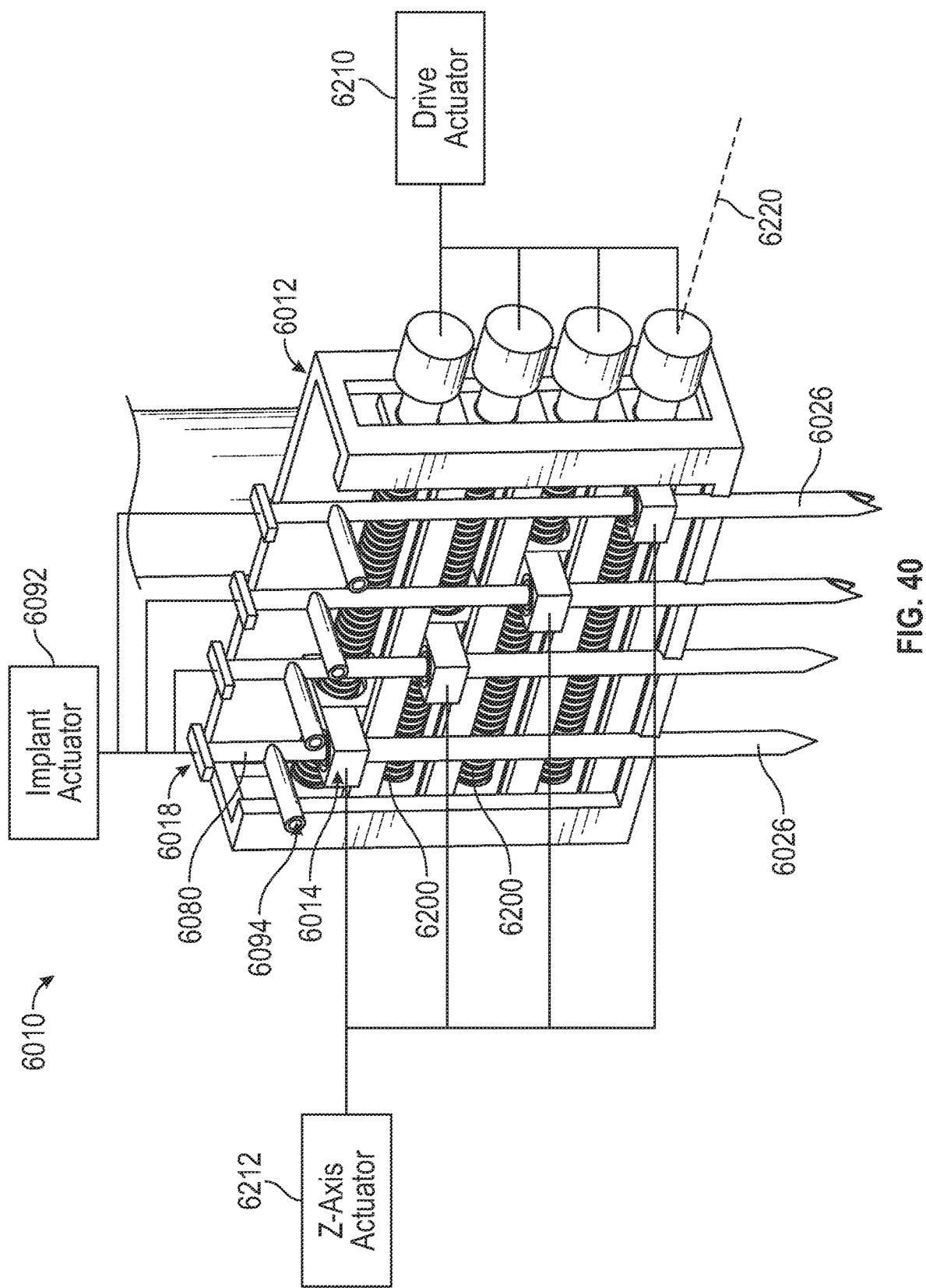

SYSTEMS AND METHODS FOR A HAIR TRANSPLANT SYSTEM WITH EXTRACTION AND IMPLANTATION NEEDLES

CROSS-REFERENCE TO RELATED APPLICATIONS

This application is a national stage application filed under 35 U.S.C. § 371 of International Application No. PCT/US2021/019115, filed Feb. 22, 2021, which application is based on, claims the benefit of, and incorporates herein by reference in their entirety U.S. Provisional Patent Application Ser. No. 62/979,504, filed on Feb. 21, 2020, and entitled "Systems and Methods for a Hair Transplant System with Extraction and Implantation Needles."

BACKGROUND OF THE INVENTION

Hair loss is one of the most psychological issues that is affecting 80 million people in the United States alone. As a result, the commercial market for addressing hair loss is a multi-billion dollar industry, from drug therapies to hair transplantation.

Hair transplantation is a procedure that involves implanting multiple hair follicles or follicular units, from a donor site of a donor, into a recipient site of a patient. There are two types of hair transplantation procedures: Follicular Unit Transplantation ("FUT"), and Follicular Unit Extraction ("FUE"). In FUT, a long strip of skin is cut from the donor site (e.g., usually back of the head) and from the cut skin, the hair follicles are separated. For implanting, small holes are made at the recipient site and the separated hair follicles are inserted into them one at a time. This procedure requires highly skilled surgeons and technicians and leaves a long scar where the skin was cut. In FUE, each hair follicle is identified, and small holes are made using coring punches around the hair follicle and then removing the hair follicle from the donor site one at a time. For implanting, small holes are made at the recipient site and each hair follicle is inserted in to the holes. The holes are then allowed to heal around the implanted hair follicle.

Presently, this procedure is generally performed using differing tools for extraction of the hair follicle, creation of the small opening, and implantation of the hair follicle. Further, the procedure is typically done by implanting a single hair follicle at a time. A single hair transplant session may implant anywhere from 1,500 to 3,000 hair follicles. With each hair follicle taking as long as twenty seconds to transplant, each session is very labor intensive and can last as long as eight to twelve hours. As such, the current process for hair transplantation is tedious, time-consuming, and costly. Therefore, it would be advantageous to have systems and methods to reduce the hair transplantation surgery (FUE) time and increase hair transplantation efficiency.

SUMMARY

The present disclosure overcomes the above and other drawbacks by providing systems and methods for efficient hair transplants using a hair transplant device that can extract a hair follicle from a donor site using an extraction unit, create an opening in a recipient site with an implantation unit, and implant the hair follicle within the opening in the recipient site. In some configurations, the systems and methods of the present disclosure allow the extraction and implantation units to be independently adjustable, as well as separable from each other. The systems and methods of the present disclosure are capable of extracting multiple hair follicles from the donor site simultaneously, creating multiple openings in the recipient site simultaneously, and implanting multiple hair follicles within the multiple openings in the recipient site. Systems and methods are provided for improved hair transplant procedures that increase extraction speed, opening speed, and implantation speed, thereby increasing efficacy and reducing cost.

In accordance with one aspect of the disclosure, a hair transplant device is provided. The hair transplant device includes an extraction unit including a coring needle configured to extract at least one hair follicle from a donor site, an implanting unit removably coupled to the extraction unit, the implanting unit including a splitting needle configured to create an opening in a recipient site, a housing coupled to the extraction unit, and a user interface extending from the housing and moveable relative to the housing. When the extraction unit is assembled with the implanting unit, the coring needle and the splitting needle are arranged along a common axis and the coring needle and the splitting needle are axially separated such that the user interface can be displaced to drive the hair follicle from within the coring needle into the opening in the recipient site to implant the hair follicle.

In accordance with one aspect of the disclosure, a hair transplant device is provided. The hair transplant device includes an extraction unit configured to extract at least one hair follicle from a donor site and an implanting unit removably coupled to the extraction unit. The extraction unit includes a coring needle having a first cutting end configured to form a core from a donor site and a first coupling end opposite the first cutting end. The implanting unit includes a splitting needle having a second cutting end configured to form an opening into a recipient site and a second coupling end opposite the second cutting end. The hair transplant device also includes a housing coupled to the extraction unit, a pin moveable relative to the housing and configured to be slidably received within the coring needle. A coupling is configured to connect the coring needle and the splitting needle together at the first cutting end and the second coupling end, respectively, when the extraction unit is assembled with the implanting unit.

In accordance with one aspect of the disclosure, a method of performing a hair transplant procedure is provided. The method includes driving a coring needle to engage a donor site to arrange a hair follicle within a coring lumen of the coring needle, coupling a splitting needle to a cutting end of the coring needle, driving the splitting needle to engage a recipient site to create an opening in the recipient site, and engaging a user interface to displace a pin axially aligned with the coring needle and the splitting needle to displace the hair follicle from within the coring lumen into the opening in the recipient site to implant the hair follicle.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 7 is a side profile view of a coupling unit for coupling the extraction and implanting needles according to one aspect of the present disclosure.

FIG. 8 is a cross sectional exploded view of the coupling unit of FIG. 7.

FIG. 9 is a profile view of a coupling unit for coupling extraction and implanting needles of different diameters.

FIG. 10 is a profile view of a coupling unit for coupling extraction and implanting needles of different diameters.

FIG. 12 is a schematic illustration of hair follicle extraction in accordance with one aspect of the present disclosure.

FIG. 13 is a schematic illustration of coupling an implanting needle to an extraction needle with a coupling unit illustrated as translucent.

FIG. 25 is an illustration of hair follicle extraction utilizing the hair transplant device of FIG. 21.

FIG. 26 is an illustration of coupling an implanting unit to an extraction unit utilizing the hair transplant device of FIG. 21.

FIG. 27 is an illustration of coupling a casing the hair transplant device of FIG. 21.

FIG. 28 is an illustration of a first step of hair follicle implanting utilizing the hair transplant device of FIG. 21.

FIG. 29 is an illustration of a second step of hair follicle implanting utilizing the hair transplant device of FIG. 21.

FIG. 30 is an illustration of a third step of hair follicle implanting utilizing the hair transplant device of FIG. 21.

FIG. 37 is an illustration of a first step of hair follicle implanting utilizing the hair transplant device of FIG. 33.

FIG. 38 is an illustration of a second step of hair follicle implanting utilizing the hair transplant device of FIG. 33.

FIG. 39 is an illustration of a third step of hair follicle implanting utilizing the hair transplant device of FIG. 33.

FIG. 40 is an illustration of hair transplant device including a linear array of coring needles.

DETAILED DESCRIPTION OF THE INVENTION

Figure 1:
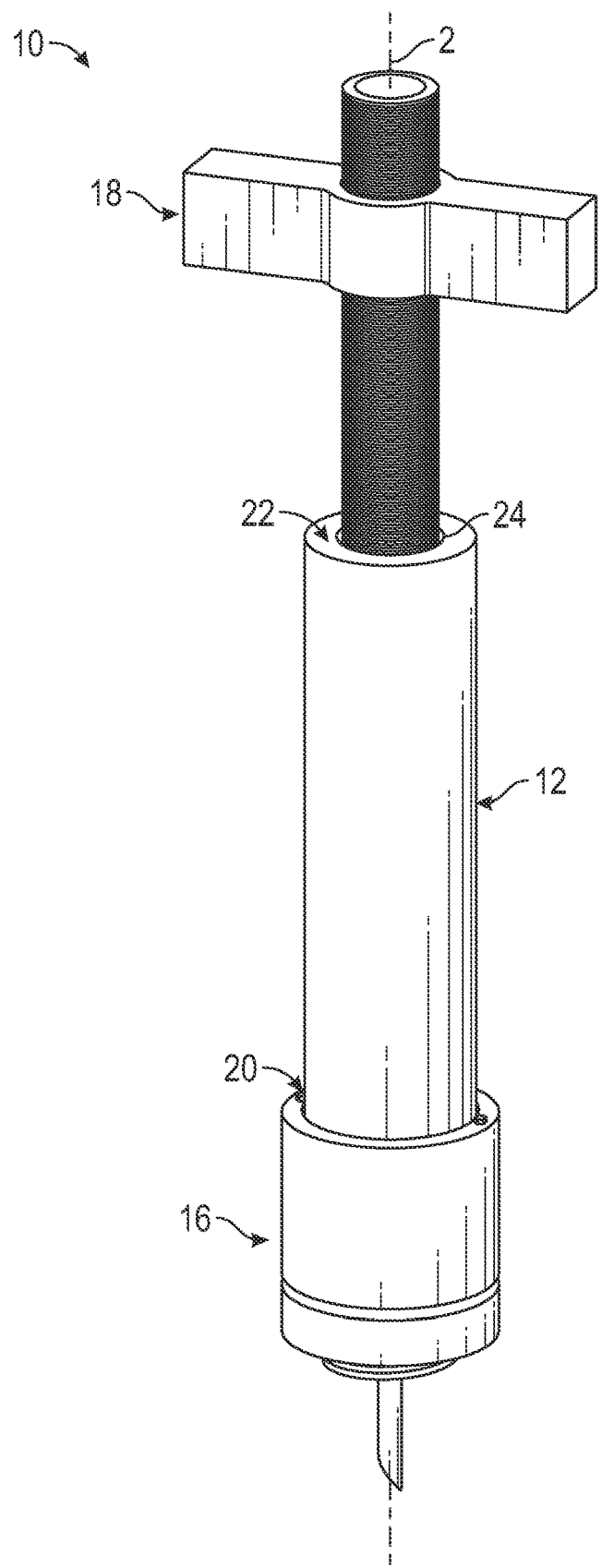
FIG. 1 is a perspective view of a hair transplant device including an implanting and extraction unit in accordance with one aspect of the present disclosure.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

The word "exemplary" is used herein to mean serving as an example, instance, or illustration. Any aspect or design described herein as "exemplary" is not necessarily to be construed as preferred or advantageous over other aspects or designs. Further, the terms axial, radial, and circumferential used herein refer to directions relative to a central axis 2 (see FIG. 1).

As will be described herein, the present disclosure provides systems and methods for transplanting hair follicles from a donor site to a recipient site using a hair transplant device. The hair transplant devices described herein include an extraction unit configured to extract at least one hair follicle from a donor site and an implanting unit removably coupled to the extraction unit, the implanting unit including configured to form an opening into a recipient site. According to some embodiments, a housing is coupled to the extraction unit and a pin moveable relative to the housing is configured to be slidably received within the extraction and implantation units to aid the insertion of a transplanted hair follicle into a recipient site. The hair transplant device also includes a coupling configured to connect a coring needle of the extraction unit and a splitting needle of the implanting unit together, in an end-to-end fashion, when the extraction unit is assembled with the implanting unit.

Figure 2:
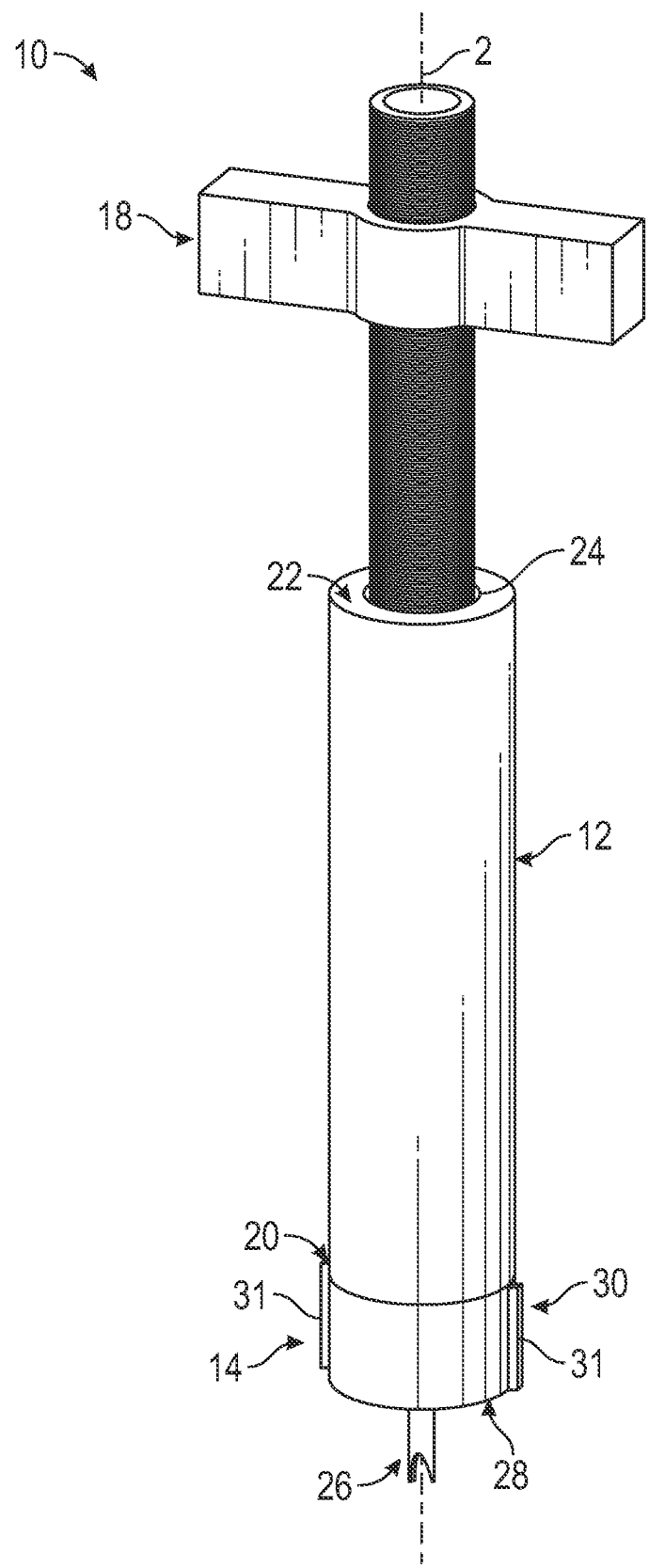
FIG. 2 is a perspective view of the hair transplant device of FIG. 1 with the implanting unit removed from the extraction unit.

Referring now to the drawings wherein like reference numerals correspond to similar elements throughout the several views and, more specifically, referring to FIGS. 1 and 2, a hair transplant device 10 for extracting hair follicles from a donor site of a donor and implanting them into a recipient site of a patient is illustrated. These hair follicles, or follicular units, can contain a single hair or multiple hairs grouped together. As can be seen in the illustration of FIG. 1, the hair transplant device 10 includes a housing 12, an extraction unit 14 (see FIG. 2), an implanting unit 16 removably coupled to the extraction unit 14, and a user interface 18. The housing 12 extends between a proximal end 20 (e.g., a first end adjacent the extraction unit 14) and a distal end 22 opposite the proximal end 20. The housing 12 includes an opening 24 in the distal end 22 configured to slidably receive the user interface 18.

As will be further described, the housing 12 and the implant actuator 92 may be configured for connection with an automated system, such as, for example a computer-aided manufacturing (CAM) system, for automated use of the hair transplant device 10. As will also be described, the housing 12 may additionally be configured for connection with several other similar hair transplant devices, such that an array of hair transplant devices similar to the hair transplant device 10 is provided to allow for automated extraction and/or implantation of multiple hair follicles in series or simultaneously. In some instances, the housing 12 may additionally or alternatively be configured for manual manipulation (e.g., can include a handle).

As best illustrated in FIG. 2, the hair transplant device 10 is shown with the implanting unit 16 removed from the extraction unit 14. The extraction unit 14 is coupled to the housing 12 proximate the proximal end 20. The extraction unit 14 includes an extraction/coring needle 26 coupled to and extending from a lower end 28 of the extraction unit 14. The extraction unit 14 can also include one or more guideways 30 configured to engage the implanting unit 16 to prevent the implanting unit 16 from rotating relative to the extraction unit 14 when coupled therewith. In the illustrated embodiment, the guideways 30 are configured as protrusions 31 extending radially outward from the extraction unit 14. The protrusions 31 extend axially along an outer surface of the extraction unit 14. In the illustrated embodiment, the protrusions 31 are arranged on circumferentially opposing sides of the extraction unit (e.g., circumferentially separated by about 180 degrees). In other embodiments, extraction units can include a plurality of guideways. In some embodiments, the guideways can be circumferentially separated by more or fewer than 180 degrees (e.g., 45 degrees, 90 degrees, 120 degrees, 270 degrees, etc.).

Figure 3:
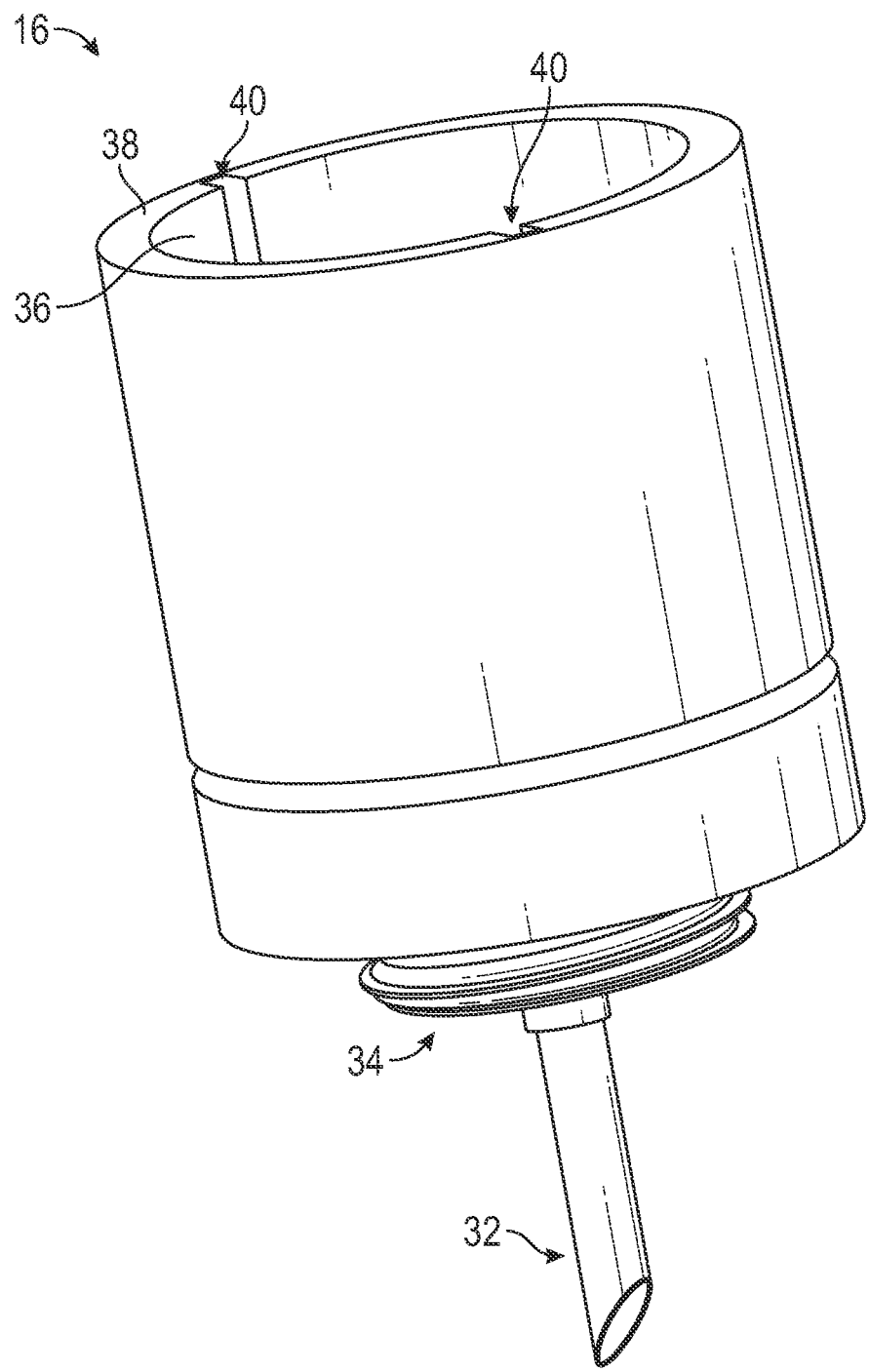
FIG. 3 is a perspective view of the implanting unit of FIG. 1.

Referring now to FIGS. 1 and 3, the hair transplant device 10 is shown with the implanting unit 16 installed on the extraction unit 14. The implanting unit 16 is removably coupled to the extraction unit 14 and at least partially enveloping the extraction unit 14. The implanting unit 16 similarly includes an implanting/splitting needle 32 coupled to and extending from a lower end 34 of the implanting unit 16. The implanting unit 16 can also include a recess 36 configured to receive the extraction unit 14 therein. In the illustrated embodiment, the recess 36 extends axially into the implanting unit 16 from a top end 38 thereof. The recess 36 includes one or more slots 40 configured to engage the corresponding guideways 30 on the extraction unit 14 when the implanting unit 16 is coupled with the extraction unit 14. In the illustrated embodiment, the slots 40 extend radially outward from an inner surface of the recess 36. The slots 40 extend axially along the inner surface of the recess 36. In the illustrated embodiment, the number and spacing of the slots 40 on the implanting unit 16 corresponds to the number and spacing of the guideways 30 on the extraction unit 14.

Figure 4:
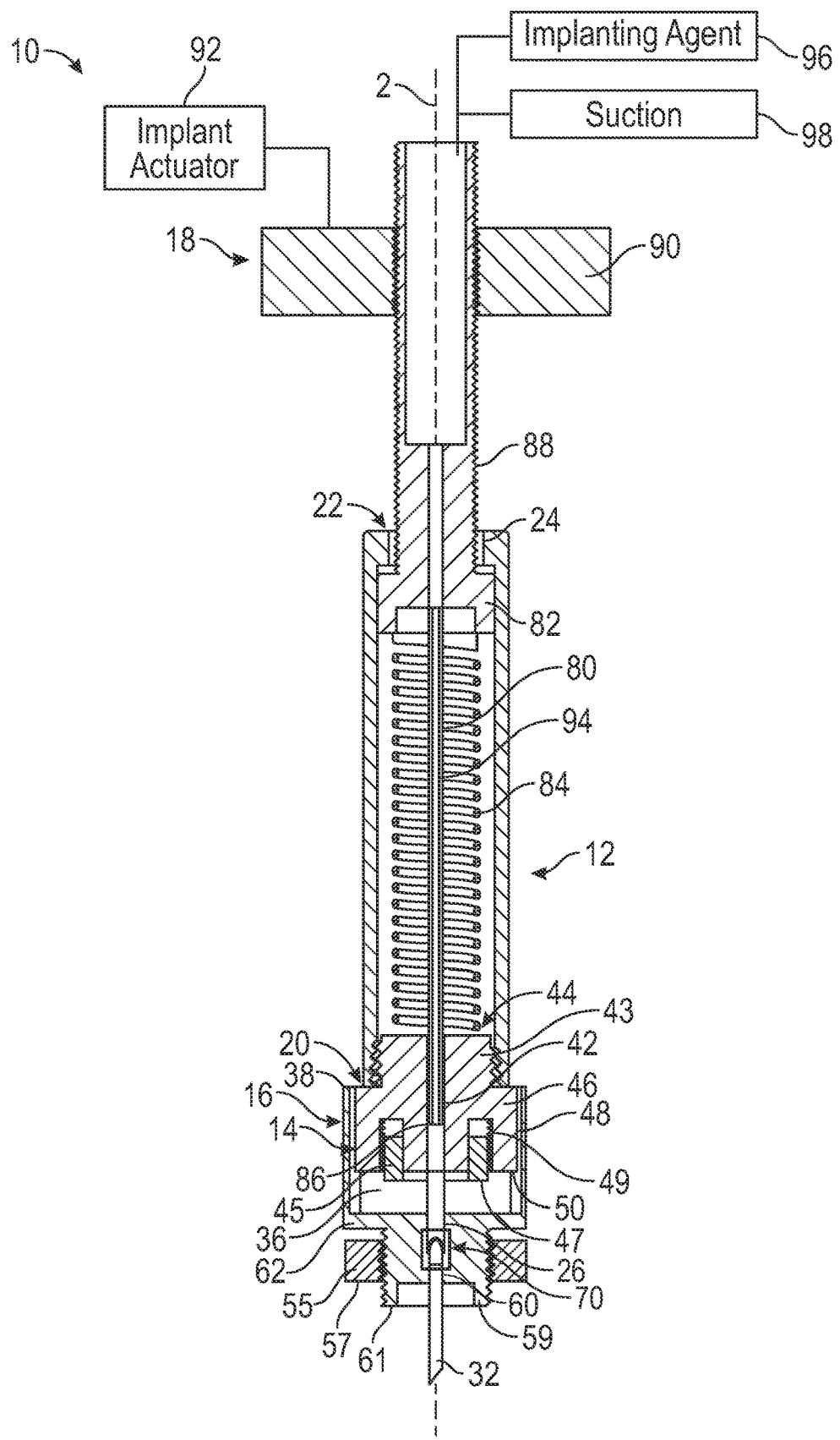
FIG. 4 is a cross section of the hair transplant device of FIG. 1.

Looking to FIG. 4, the extraction unit 14 defines a coring lumen 42 extending axially through both the extraction unit 14 and the coring needle 26 coupled thereto. The coring lumen 42 is centrally disposed within and may extend through the extraction unit 14, from an upper surface 44 of the extraction unit 14 through a distal end of the coring needle 26. The extraction unit 14 can include a coring flange 46 extending radially outward from the coring lumen 42, terminating at an outer surface 48. The outer surface 48 of the coring flange 46 slidably engages an inner surface of the recess 36 within the implanting unit 16. The extraction unit 14 is coupled to the housing 12. In the illustrated embodiment, the extraction unit 14 includes a threaded boss 43 protruding axially away from the coring flange 46. The threaded boss 43 includes external threads configured to engage internal threads at the proximal end 20 of the housing 12.

The extraction unit 14 further includes an extraction stop 45 moveable relative to the distal end of the coring needle 26. The extraction stop 45 is configured to adjust a coring depth such that, during extraction of the hair follicle, contacts a surface of the donor site at a predetermined coring depth. For example, in the illustrated embodiment, the extraction stop 45 includes a first interface surface 47, and a positioning of the extraction stop 45 positions the first interface surface 47 a predetermined distance away from the distal end of the coring needle 26. In that way, the coring depth can be defined by the distance between the distal end of the coring needle 26 and the first interface surface 47.

In the illustrated embodiment, the extraction stop 45 defines an annular shape and is configured to be threadably engaged with the extraction unit 14. Specifically, the extraction unit 14 includes a threaded annular recess 49 configured to receive the extraction stop 45. In the illustrated embodiments, with the extraction stop 45 adjusted to provide a maximum coring depth (e.g., with the extraction stop threaded into the extraction unit 14 such that the first interface surface 47 is above the lower surface 50), the lower surface 50 of the extraction unit 14 can provide the interface surface between the hair transplant device 10 and the donor site.

Figure 5:
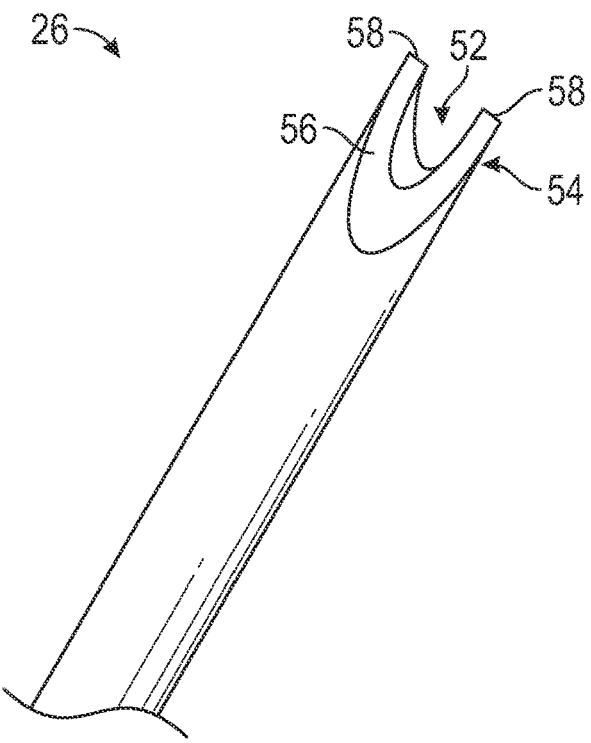
FIG. 5 is a perspective view of a cutting end of an extraction needle.

The coring needle 26 extends axially away from a lower surface 50 of the coring flange 46, and when the implanting unit 16 is assembled onto the extraction unit 14, at least partially engages a lumen in the implanting unit 16. As best illustrated in FIG. 5, the coring needle 26 may be formed as a hollow needle, with the coring needle lumen 52 extending therethrough. Further, the coring needle 26 may include a first distal cutting end 54. The distal cutting end 54 is configured to cut into the donor site to form a core in order to extract a hair follicle within the core. The first distal cutting end 54 may be disposed completely outside of the housing 12 and include a pair of angled surfaces 56 that angle toward each other, intersecting at the distal end of the coring needle 26. Accordingly, the pair of angled surfaces 56 form a pair of cutting edges 58 disposed on opposite sides of the coring needle lumen 52. The pair of cutting edges 58 are effectively aligned across the coring needle 26, such that they both extend radially from an inner surface of the coring needle 26 to an outer surface of the coring needle 26. As such, the coring needle 26 can be configured to cut into tissue by driving the coring needle 26 into the tissue, without needing to rotate the coring needle 26.

Looking back at FIG. 4, the implanting unit 16 defines a splitting lumen 60 centrally disposed within and extending all the way through the implanting unit 16 to a distal end of the splitting needle 32. In the illustrated embodiment, the coring and splitting lumens 42, 60 are axially aligned such that fluid communication can be provided from the distal end of the splitting needle 32 into the coring lumen 42. The implanting unit 16 includes a splitting flange 62 extending radially outward at a medial portion of the implanting unit 16, thereby defining a base of the recess 36.

The implanting unit 16 further includes an implanting stop 55 moveable relative to the distal end of the splitting needle 32. The implanting stop 55 is configured to adjust an implanting depth such that, during implantation of the hair follicle, contacts a surface of the recipient site at a predetermined implanting depth. For example, in the illustrated embodiment, the implanting stop 55 includes a second interface surface 57, and a positioning of the implanting stop 55 positions the second interface surface 57 a predetermined distance away from the distal end of the splitting needle 32. In that way, the implanting depth can be defined by the distance between the distal end of the splitting needle 32 and the second interface surface 57.

In the illustrated embodiment, the implanting stop 55 defines an annular shape and is configured to be threadably engaged with the implanting unit 16. Specifically, the implanting unit 16 includes a threaded boss 59 extending axially away from the splitting flange 62 that is configured to receive the implanting stop 55. In the illustrated embodiments, with the implanting stop 55 adjusted to provide a maximum implanting depth (e.g., with the implanting stop threaded onto the implanting unit 16 such that the second interface surface 57 is above a lower surface 61 of the implanting unit), the lower surface 61 of the implanting unit 16 can provide the interface surface between the hair transplant device 10 and the recipient site.

In the illustrated embodiment, the implanting depth and the coring depth are independently adjustable. For example, adjustment of the coring depth via the extraction stop 45 imparts no effect on the implanting depth. Similarly, adjustment of the implanting depth via the implanting stop 55 imparts no effect on the coring depth. The independent adjustment of each of the implanting and coring depths allows for a more versatile hair transplant device 10.

Figure 6:
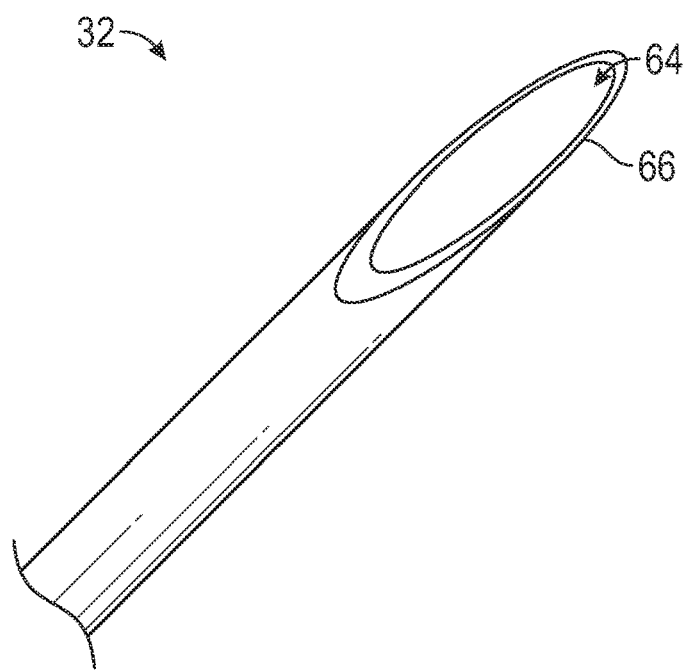
FIG. 6 is a perspective view of a cutting end of an implanting needle.

The splitting needle 32 is axially separated from the coring needle 26 and extends axially away from the splitting flange 62. In the illustrated embodiment, the splitting needle 32 and the coring needle 26, as well as the coring and splitting lumens 42, 60, are axially aligned along a common central axis (e.g., axis 2). As best illustrated in FIG. 6, the splitting needle 32 is a hollow needle, with a splitting needle lumen 64 extending therethrough. Further, the splitting needle 32 includes a second distal cutting end 66 that is angled relative to a central axis of the splitting needle 32 (e.g., axis 2, FIG. 4). The distal cutting end 66 of the splitting needle 32 is configured to form an opening in a recipient site in order to implant the extracted core. The second distal cutting end 66 has a specific cutting geometry (e.g., the angle of the distal cutting edge) that can prevent tissue from entering the splitting needle 32 while the splitting needle 32 cuts into skin by piercing the skin and gradually pushing the tissue apart, similar to the function of a hypodermic needle.

Referring back to FIG. 4, in the illustrated embodiment, the coring needle 26 and the splitting needle 32 do not axially overlap. The hair transplant device 10 also includes a coupling unit 70 arranged between the coring needle 26 and the splitting needle 32. According to the illustrated embodiment, the coupling unit 70 can be integrally formed into the implanting unit 16. According to other embodiments, the coupling unit 70 can be rigidly coupled to the splitting needle 32. According to other embodiments, the coupling unit 70 can be separable from each of the coring needle 26 and the splitting needle 32.

As best illustrated in FIGS. 7 and 8, the coupling unit 70 is configured to provide an end-to-end coupling of the coring and splitting needles 26, 32. For example, the coring needle 26 includes the distal cutting end 54 (e.g., a first cutting end) and a first coupling end 71 opposite the distal cutting end 54. The coupling unit 70 is configured to receive the distal cutting end 54 of the coring needle 26 at a first end 73 of the coupling unit 70. The first coupling end 71 configured for coupling to the extraction unit 14. The splitting needle 32 includes the distal cutting end 66 (e.g., a second cutting end) and a second coupling end 72 opposite the distal cutting end 66. The coupling unit 70 is configured to receive the second coupling end 72 of the splitting needle 32 at an opposing second end 75 of the coupling unit 70.

The internal aspect of the coupling unit 70 can include a matching contour to the coring needle 26 and the splitting needle 32 where they engage the coupling unit 70 to allow smooth transition of a skin core through the coupling unit 70 or, if going through needles of varying diameters, the coupling unit can have a tapered interior. For example, in the illustrated embodiment, the coupling unit 70 can be configured as a cylindrical sleeve including a hollow core 76 extending from the first end 73 through to the second end 75. When assembled, a continuous lumen can be defined by the coring needle 26, the coupling unit 70, and the splitting needle 32. The hollow core 76 can define a stepped profile including recesses entering from both ends to accommodate the coring and splitting needles 26, 32. For example, according to the illustrated embodiment, in order to provide a smooth and seamless transition, the first end 73 of the coupling unit 70 can include a coring needle recess 77 defining a shape complementary to the distal cutting end 54 of the coring needle 26, such that an inner diameter D1 of the coring needle 26 matches an inner diameter of the coupling unit 70. Similarly, the second end 75 of the coupling unit 70 can include a splitting needle recess 78 defining a shape complementary to the second coupling end 72 of the splitting needle 32, such that an inner diameter D2 of the splitting needle 32 matches an inner diameter of the coupling unit 70. That is, the inner diameter between the coring needle recess 77 and the splitting needle recess 78 can define a diameter equal to the inner diameters of the coring and splitting needles 26, 32.

In the illustrated embodiment, the inner diameter D1 of the coring needle 26 and the inner diameter D2 of the splitting needle 32 are the same. That is, the coring needle 26 defines a first diameter that is equal to a second diameter defined by the splitting needle 32. According to other embodiments, the diameters of the coring and splitting needles 26, 32 may be different. For example, referring to FIGS. 9 and 10, alternative embodiments of a coupling unit 70a, 70b are illustrated. In the embodiment illustrated in FIG. 9, the coring needle 26a defines a first diameter D1 and the splitting needle 32a defines a second diameter D2, where the first diameter D1 is smaller than the diameter D2. In the embodiment illustrated in FIG. 10, the coring needle 26b defines a first diameter D1 and the splitting needle 32b defines a second diameter D2, where the first diameter D1 is larger than the diameter D2. In such an embodiment, the hair follicles can be extracted with the larger coring needles 26b and implanted with the smaller splitting needle 32b. This method can help to increase the density of hair follicles per area at the recipient site. As illustrated, in any embodiment of the coupling unit 70a, 70b, the hollow core 76a, 76b is configured to provide a smooth and seamless transition from the coring needle 26a, 26b to the splitting needle 32a, 32b.

Referring back to FIG. 4, the user interface 18 is disposed to extend from the housing 12, near the distal end 22, and is partially enveloped by the housing 12. The user interface 18 may include a pin 80, a head 82, and a spring 84. The pin 80 extends axially away from the head 82, and is disposed partially within the coring lumen 42 of the extraction unit 14. The pin 80 can be selectively actuated within the coring lumen 42 by axial movement of the user interface 18. The illustrated pin 80 includes a distal tip surface 86 that is flat. However, in some instances, the distal tip surface 86 could alternatively be round, pointed, or any other suitable shape. The user interface 18 includes a user interface body 88 extending axially away from the head 82 and extends outside of the housing 12 through the opening 24. A user interface flange 90 is coupled to the user interface body 88 (e.g., via the threads thereon) and presents a surface upon which a force or pressure can be exerted by a user to control actuation of the system. In some instances, the user interface flange 90 may be configured for connection with the automated system, such that the user interface 18 can be moved automatically. For example, in the illustrated embodiment, the user interface 18 can be coupled to and actuated by an implant actuator 92 (e.g. solenoid actuator) to axially push the pin 80 to the scalp. The implant actuator 92 may have enough force to drive a single or multiple elements or needles into the tissue. In other instances, the flange 90 may additionally or alternatively be configured for other kinds of automated or manual manipulation.

The spring 84 is disposed around the pin 80, between a lower surface of the head 82 and the upper surface 44 of the extraction unit 14. The spring 84 is configured to compress when the user interface 18 is advanced axially towards the extraction unit, thereby providing a resistive force against the user interface 18.

Figure 16:
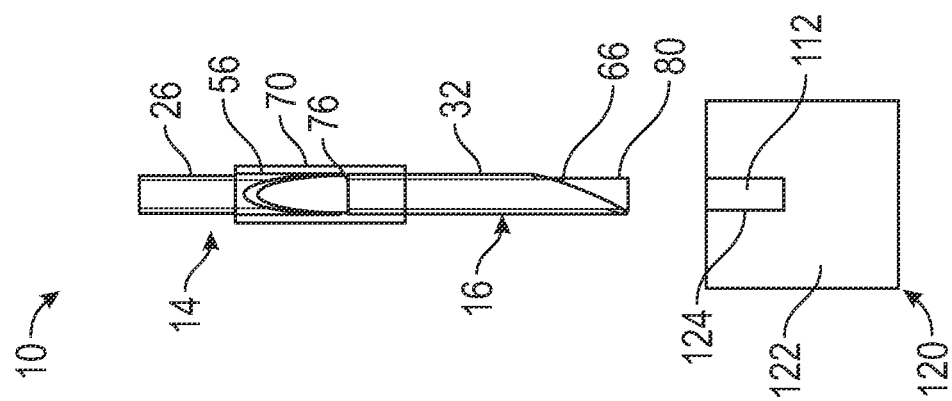
FIG. 16 is a schematic illustration of a third step of hair follicle implanting with the coupling unit illustrated as translucent.
Figure 15:
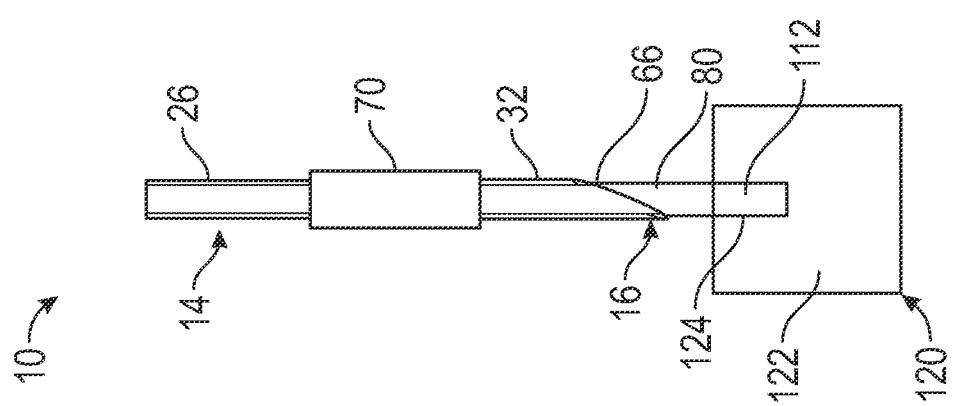
FIG. 15 is a schematic illustration of a second step of hair follicle implanting.
Figure 14:
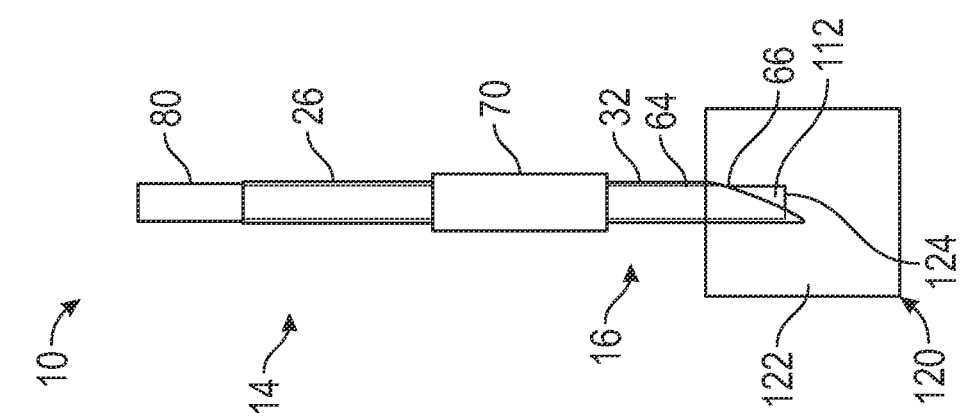
FIG. 14 is a schematic illustration of a first step of hair follicle implanting.

The user interface 18 is selectively movable between a retracted position (shown in FIGS. 4, 12, and 13) and an inserted position (shown in FIGS. 14-16). In the retracted position, the user interface 18 is arranged, such that only a small portion of the pin 80 is disposed within the coring lumen 42 of the extraction unit 14. That is, in the retracted position, the pin 80 does not extend past the distal cutting end 54 of the coring needle 26. In the inserted position, the user interface 18 is moved axially a predetermined amount, such that the pin 80 is inserted through the coring lumen 42, past the distal cutting end 54 of the coring needle 26, through the coupling unit 70, such that the distal tip surface 86 of the pin 80 is disposed proximate the distal cutting end 66 of the splitting needle 32. That is, the user interface 18 is configured to move a predetermined amount relative to the housing 12 to control a depth of delivery of an extracted core/hair follicle into an opening at the recipient site.

In the illustrated embodiment, the user interface 18 further includes a central lumen 94 extending axially through the head 82 to the distal tip surface 86 of the pin 80. The central lumen 94 may be included to allow for flow of a gas or a liquid through the user interface 18. The central lumen 94 is axially aligned with, and can provide fluid communication to, each of the coring lumen 42 and the splitting lumen 64 (via the coupling unit 70). The user interface body 88 may be coupled to a fluid delivery system and/or a fluid aspiration system to provide gas or liquid through the user interface 18 and/or to suction gas or liquid through the user interface 18. For example, the central lumen 94 can be in fluid communication with an implanting agent source 96 configured to provide an implanting agent to the central lumen 94 for use during implanting of the extracted core/hair follicle at the recipient site. For example, glycerol or polyethylene glycol can be used an implanting agent, which can act as a non-toxic lubricant. Additionally or alternatively, the central lumen 94 can be in fluid communication with a suction source 98 configured to provide suction at the tip of the pin 80 for use during extraction of a core/hair follicle. For example, suction can be used to effectuate the extraction of the core after the coring needle 26 has cut into the donor site.

Figure 11:
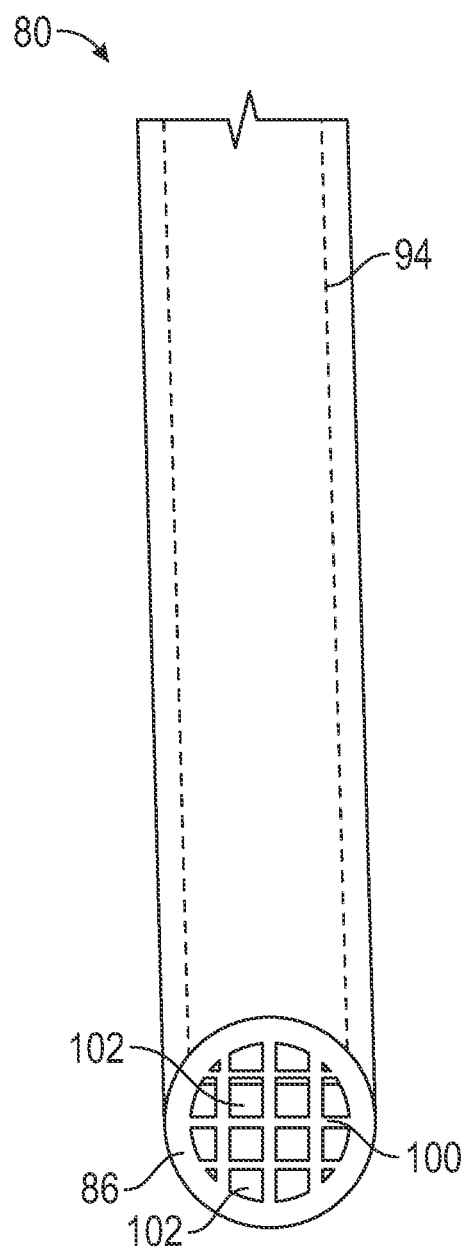
FIG. 11 is a perspective view of an end of a pin in accordance with one aspect of the present disclosure.

Referring to FIG. 11, the distal tip surface 86 of the pin 80 can include a mesh 100. The mesh 100 can be configured to prevent the core extracted from the donor site from being pulled into the central lumen 94 of the pin 80. For example, if suction is applied to the central lumen 94 (e.g., via the suction source 98, FIG. 4), the mesh 100 can provide a surface that allows suction therethrough, but does not allow the passage of objects such as the extracted core. The mesh 100 can define a porous surface including a plurality of holes 102.

Now that the general structure of the hair transplant device 10 has been described above, exemplary methods of use will be described below. It should be noted that the methods of use described below are given as examples, and are not meant to be limiting in any way.

The hair transplant device 10 can be used to perform multiple different procedures to complete a hair transplant operation on a patient. For example, the device 10 is designed to perform an extraction procedure (shown in FIG. 12); a coupling procedure (shown in FIG. 13); an opening procedure (shown in FIG. 14); and an implantation procedure (shown in FIGS. 14-16). Although any one of these three procedures can be performed individually by the hair transplant device 10, the hair transplant device 10 allows for these procedures to be done sequentially and repetitively. That is, the hair transplant device 10 can first be used to extract a core containing a hair follicle from a donor site of a donor during an extraction procedure. The hair transplant device 10 can then, while still containing the core from the donor site, be used to create an opening that is configured to receive the core in a recipient site of the patient. Then, the hair transplant device 10 can be used to implant the core from the donor site into the recipient site. Finally, once the hair follicle has been implanted into the recipient site, the hair transplant device 10 can be used to repeat this process again and again to complete the hair transplant operation. This process may be repeated, for example, tens, hundreds, or even thousands of times.

In the following figures, many aspects of the hair transplant device 10 have been hidden to provide clarity to the process, and it is to be understood that the hair transplant device 10 previously described (as well as all other embodiments to follow) can utilize the foregoing procedure. FIG. 12 illustrates the hair transplant device 10 being used during an extraction procedure. According to some procedures, before starting the hair transplant process, the hair can be cut or slipped to a required height (e.g., about 1-2 millimeters). As illustrated, the hair transplant device 10 can first be placed above a donor site 110 of a donor in an extraction configuration, where the implanting unit 16 removed from the device (e.g., FIG. 2) and the pin 80 is in the retracted position. As such, the coring needle 26 is exposed outside of the extraction unit 14.

With the pin 80 in the retracted position, the coring needle 26 can then be inserted into the donor site 110 around a skin core 112, with the distal cutting end 54 of the coring needle 26 cutting through the surrounding donor tissue 114, as illustrated in FIG. 12. During the extraction procedure, in the instances where the central lumen 94 of the pin 80 (see FIG. 4) is coupled to a suction source 98, suction or negative pressure may be provided through the central lumen 94 of the pin into the coring needle lumen 52 when removing the coring needle 26 to provide additional control and force for removing the skin core 112 from the donor site 110. In some cases, the suction source 98 is activated after insertion of the hair transplant device 10. In other cases, the suction source 98 is activated before insertion of the hair transplant device 10. In any case, the mesh 100 (shown in FIG. 11) at the distal end of the pin 80 prevents the skin core 112 from being drawn into the central lumen 94 of the pin 80. The suction can also retain the skin core 112 within the coring needle 26 (see FIG. 13) after the coring needle 26 has been removed from the donor site 110 and during the transition to a recipient site. Said differently, the mesh 100 on the distal end of the pin 80 is configured to prevent the skin core 112, likely containing a hair follicle, from being drawn past a predetermined position within the coring needle 26.

The coring needle lumen 52 may define an inner diameter that is larger than the average distance between hair follicles within the donor site 110 (i.e., approximately 1 mm), such that the coring needle 26 extracts at least one (or more) hair follicles contained in the skin core 112 when inserted into the donor site. As such that the hair transplant device 10 should always extract skin cores 112 containing, along with other skin components (e.g., epidermis, collagen, elastin, blood vessels, etc.), at least one hair follicle having at least one hair (not shown) during the extraction procedure.

In the illustrated procedure, the coring needle 26 is inserted substantially perpendicular to the donor site 110. According to some procedures, the coring needle 26 can be inserted at varying angles to extract the skin core 112 having the hair follicle in a desired orientation. This variation of the angle of insertion can be controlled using the automated system described above. As illustrated in FIG. 13, after insertion, the coring needle 26 can then be removed from the donor site 110, still containing the skin core 112 within the coring needle 26, thereby leaving a small opening in the donor site 110.

Next, as illustrated in FIG. 13, the implanting unit 16 can be coupled to the extraction unit 14. Specifically, the splitting needle 32 can be coupled to the coring needle 26 via the coupling unit 70. According to some procedures, the implantation unit 16 can be pre-inserted at a recipient site. For example, the implanting unit 16 can either be coupled along with the extraction unit 14 to implant hair directly into the recipient site or the implantation unit 16 can be pre-positioned at the recipient site, and then the extraction unit 14 can be coupled to the pre-positioned implanting unit 16, which can allow for faster transplantation of the hair follicles.

FIG. 14, in part, illustrates the hair transplant device 10 being used during an opening procedure. As illustrated, the implanting unit 16, either installed onto the hair transplant device 10 or individually if pre-positioning. If installed onto the extraction unit 14, the hair transplant device 10 can first be placed above a recipient site 120 of a recipient in an opening configuration. In the opening configuration, the pin 80 remains in the retracted position. As such, the distal cutting end 66 of the splitting needle 32 is exposed. With the hair transplant device 10 in the opening configuration, or if pre-positioning the implanting unit individually, the splitting needle 32 can be inserted into the recipient site 120, with the distal cutting edge forming an opening in the tissue 122, thereby creating a small opening 124 in the recipient site 120. Notably, though illustrated as creating this small opening 124 at an angle that is normal to a surface of the recipient site 120, the small opening 124 may be formed at an angle that is non-normal. Such non-normal angles may be facilitated by angling surfaces of the splitting needle 32 and/or orienting the splitting needle 32 to engage the recipient site 120 at a non-normal angle. According to some procedures, the suction source 98 (see FIG. 4) can be deactivated or shut off prior to the insertion of the splitting needle 32. According to other procedures, the suction source 98 can be deactivated after the insertion of the splitting needle 32, but before the implantation of the skin core 112.

FIGS. 14-16, illustrate the hair transplant device 10 being used during an implantation procedure. As illustrated in FIG. 14, with the distal cutting end 66 of the splitting needle 32 inserted into the small opening 124 created during the opening procedure, and the skin core 112 disposed within the coring needle 26, the hair transplant device 10 can be moved into the implantation configuration. In the implantation configuration, the splitting needle 32 can remain in the small opening 124, and the pin 80 can be moved into the inserted position (e.g., via the user interface 18, see FIG. 4). While the user interface 18 is moved into the inserted position, the pin 80 comes into contact with the skin core 112, thereby pushing the skin core 112 out of the coring needle 26, through the hollow coupling unit 70, through the splitting needle 32, and into the small opening 124. As such, the depth of the implantation of the skin core 112 into the small opening 124 can be controlled by the predetermined amount that the pin 80 is moved axially.

During the implantation procedure, in the instances where the central lumen 94 of the pin 80 (see FIG. 4) is coupled to an implanting agent source 96, a liquid or gaseous implanting agent may be provided through the central lumen 94 of the pin into the splitting needle lumen 64 when inserting the splitting needle 32, and/or when implanting the skin core 112 into the recipient site 120, to provide a lubricant to allow for an easier/more efficient implantation procedure. to assist in procedures, therapy, and biology related to the implantation of hair follicles. These implanting agents can be any of lubricants, flushing fluids, cleansing fluids, anesthesia fluids, medicinal fluids, or any other fluids desired to be applied through the pin 80. Specifically, the implanting agent can comprise glycerol or polyethylene glycol. Additionally or alternatively, during the implantation procedure, positive pressure may be provided through the pin 80 into the coring needle 26 to provide additional control and force for pushing the skin core 112 out of the hair transplant device 10.

After the skin core 112 has been pushed out of the coring needle 26, into the small opening 124, the assembly of the splitting needle 32, the coupling unit 70, and the coring needle 26 can be removed from the small opening 124 (e.g., via movement of the extraction unit 14 and the implanting unit 16 relative to the user interface 18), leaving the skin core 112 having the hair follicle implanted therein (FIG. 15). According to the illustrated procedure, the pin 80 is configured to remain in contact with the skin core 112 while the splitting needle 32 is withdrawn from the recipient site 120. Specifically, the pin 80 may be long enough to protrude through the coring needle 26 and distally out of the splitting needle 32 when the splitting needle 32 is coupled to the coring needle 26 via the coupling unit 70. As such, the pin 80 can provide pressure to the skin core 112 to keep the skin core 112 within the opening 124 while the coring needle 26 and the splitting needle 32 are withdrawn. In some cases, the pressure from the user interface 18 can be maintained for an extended period of time (e.g., one to two minutes) to aid in the reduction of bleeding from the recipient site 120. Next, the hair transplant device 10 can be removed from the recipient site 120 (FIG. 16).

Once implanted, the hair follicle will grow in the direction of an axis of the hair follicle. As such, extracting the skin core 112 with the coring lumen 42 of the extraction unit 14 aligned with the hair follicle axis can allow the skin core 112 to be implanted such that the hair can grow at a known angle relative to the skin surface of the recipient site 120. Accordingly, the skin core 112 can be implanted at varying angles to produce a natural-looking hair line in the recipient site 120. In some instances, the skin cores 112 can be extracted and/or implanted at angles of up to 60 degrees relative to the donor site 110 and/or the recipient site 120.

These non-normal orientations may be facilitated by the arrangement of cutting surfaces and/or arrangement of the device relative to the subject. In fully automated implementations, angle control or selection can be controlled by the automated system described above. In manual implementations, device selection from among different devices with differing geometries and/or user orientation of device during the process may control angle selection.

Figure 17:
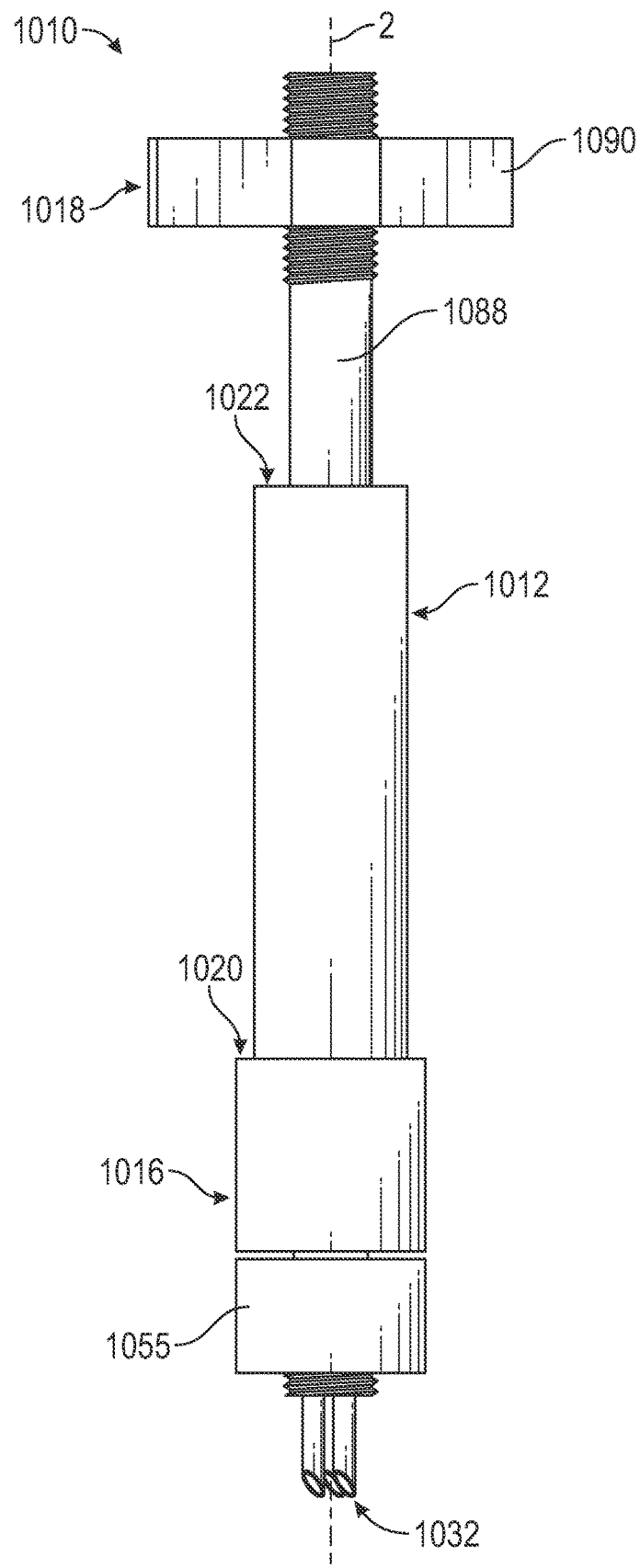
FIG. 17 is a perspective view of a hair transplant device including a plurality of implanting and extraction needles in accordance with one aspect of the present disclosure.
Figure 18:
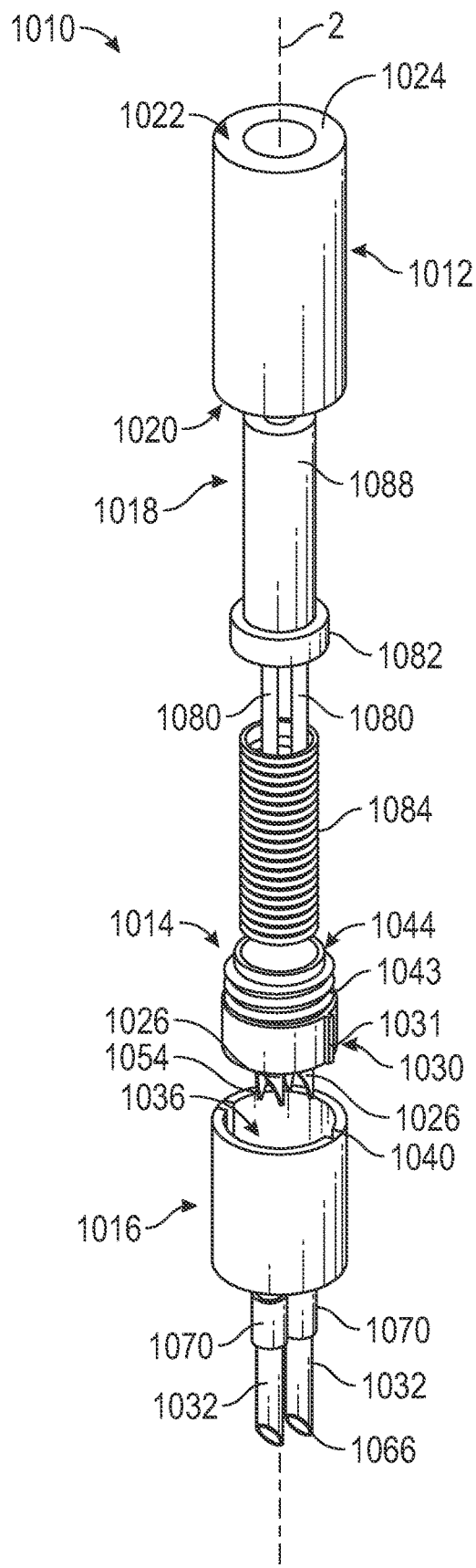
FIG. 18 is an exemplary exploded view of the hair transplant device of FIG. 17.

Referring now to FIGS. 17 and 18, a hair transplant device 1010 including a plurality of implanting/extracting needles for simultaneously extracting/implanting a plurality of hair follicles is illustrated. It is to be understood that like elements will be labeled using like reference numerals, with the exception that the numerals will be listed in the 1000's (e.g., hair transplant device 10 and hair transplant device 1010). Unless shown or described otherwise, it is to be understood that elements sharing like reference numerals are substantially similar to those previously described herein, including in their function. In the illustrated embodiment, the hair transplant device 1010 can be substantially similar to the hair transplant device 10 of FIGS. 1-16, with the exception that hair transplant device 1010 includes a plurality of coring needles 1026 and a plurality of splitting needles 1032.

With specific reference to FIG. 18, an exploded view is illustrated. It is to be understood that some aspects of FIG. 18 have been simplified for clarity (e.g., portions of the user interface 1018, such as the user interface flange 1090, the extraction and implanting stops, etc., are not shown). The hair transplant device 1010 includes an extraction unit 1014 coupled to a housing 1012 and including a plurality of coring needles 1026, each of the plurality of coring needles 1026 being configured to extract one or more hair follicles from the donor site. The hair transplant device 1010 also include an implanting unit 1016 removably coupled to the extraction unit 1014 and including a plurality of splitting needles 1032 configured to create a corresponding plurality of openings in the recipient site. In the illustrated embodiment, a plurality of coupling units 1070 are used to couple the plurality of splitting needles 1032 to the plurality of coring needles 1026. The user interface 1018 can include a plurality of pins 1080 corresponding to the number of the coring needles 1026. The plurality of pins 1080 being movable relative to the housing 1012. Each pin 1080 among the plurality of pins 1080 being configured to be received within one of the plurality of coring needles 1026. According to the illustrated embodiment, the plurality of pins 1080 are simultaneously movable via the user interface 1018. According to other embodiments, the pins 1080 are individually moveable.

In the illustrated embodiment, the plurality of coring needles 1026 and splitting needles 1032 are arranged non-linearly in a pattern or cluster. Specifically, the plurality of coring needles 1026 and splitting needles 1032 are arranged in a triangular pattern (including three splitting/coring needles arranged to form the points of a tringle). According to other embodiments, the plurality of coring needles 1026 and splitting needles 1032 can be arranged linearly (e.g., a plurality of needles arranged in a straight line).

Figure 19:
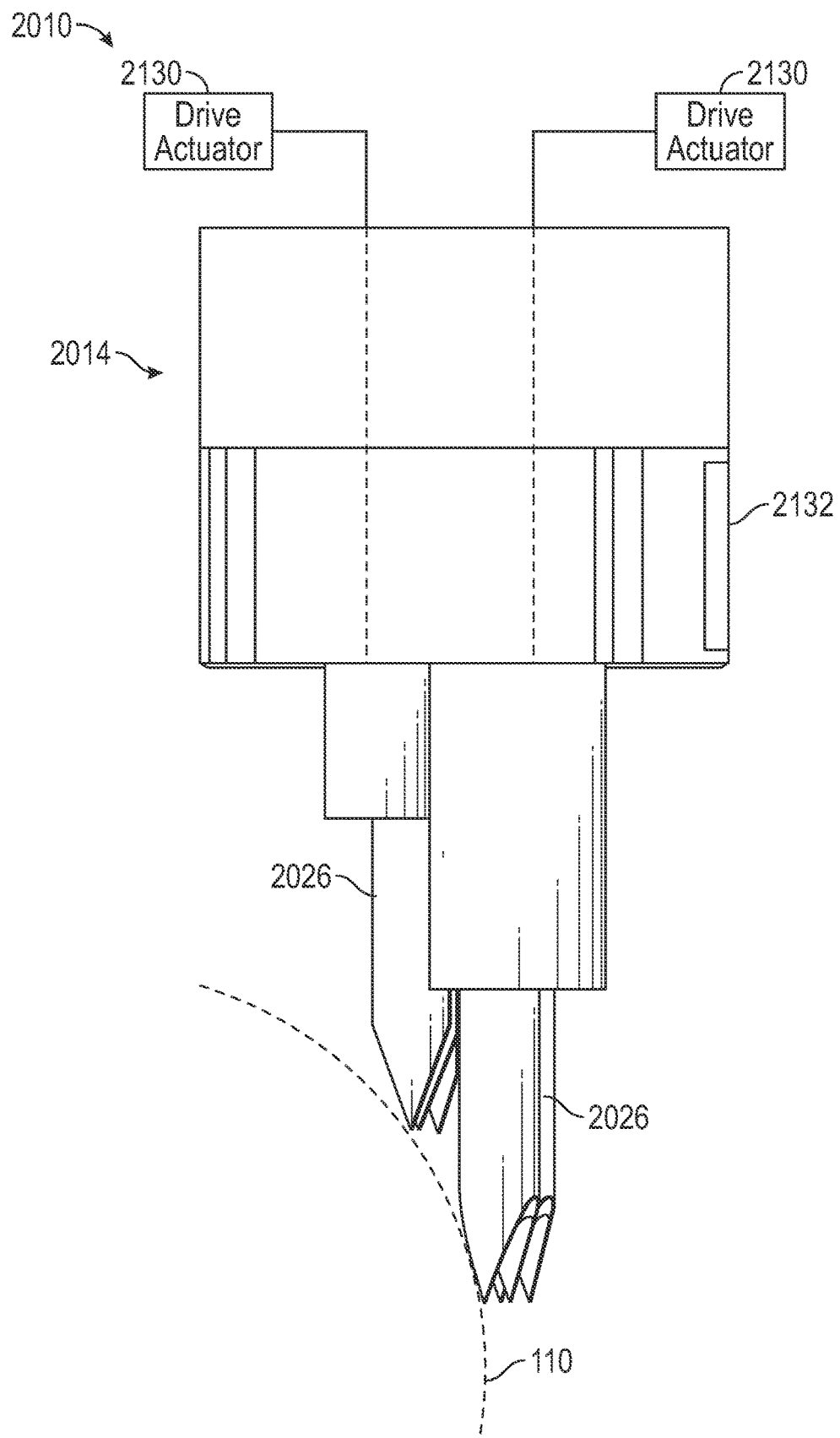
FIG. 19 is a side profile view of an extraction unit including individually adjustable extracting needles.

Referring now to FIG. 19, a hair transplant device 2010 including a plurality of implanting/extracting needles for simultaneously extracting/implanting a plurality of hair follicles is illustrated. It is to be understood that like elements will be labeled using like reference numerals, with the exception that the numerals will be listed in the 2000's (e.g., hair transplant device 10 and hair transplant device 2010). Unless shown or described otherwise, it is to be understood that elements sharing like reference numerals are substantially similar to those previously described herein, including in their function. In the illustrated embodiment, the hair transplant device 2010 can be substantially similar to the hair transplant device 1010 of FIGS. 17 and 18, with the exception that hair transplant device 2010 includes coring needles 2026 that are individually adjustable. It is to be understood that, although an extraction unit 2014 is primarily illustrated, the extraction unit 2014 could be replaced with the extraction unit 1014 of FIGS. 17 and 18.

According to the illustrated embodiment, the extraction unit 2014 can include a plurality of coring needles 2026, and an axial position of each of the coring needles 2026 can be varied to form a desired profile. For example, during the extraction procedure, the axial position of the coring needles 2026, relative to each other, can be adjusted according to the donor site 110. This can be useful at the curved surfaces of the donor site 110 (e.g., such as on a scalp), such that each of the plurality of coring needles 2026 extends into the donor site 110 at the same depth.

According to some embodiments, the axial position of each of the coring needles 2026 can be manually adjusted. According to the illustrated embodiment, drive actuators 2130 (e.g., solenoids, linear actuators, etc.) can be coupled to each of the coring needles 2026 to control an axial position thereof. This variation of the axial positioning of the coring needles 2026 via the drive actuators 2130 can be controlled using the automated system described above. The extraction unit 2014 can include a locking unit 2132 configured to lock the axial position of the splitting needles 2023 in the desired profile. According to some embodiments, the locking unit 2132 can include a spring loaded pin configured to engage a plurality of detents at distinct axial positions. According to other embodiments, the locking unit 2132 can include a threaded set screw to lock the axial position of the splitting needles 2023. According to the illustrated embodiment, the locking unit 2132 can be a lock or compression ring that applies a radially compressive force to bodies that are coupled to the splitting needles 2023 to lock the axial position of the splitting needles 2023. After going through the extraction procedure, the coring needles 2026 can be set to a position where each of the coring needles 2026 are at the same axial position and then an implantation unit (e.g., such as the implantation unit 1016 of FIG. 17) can be coupled to the extraction unit 2014 for the implantation procedure.

Figure 20:
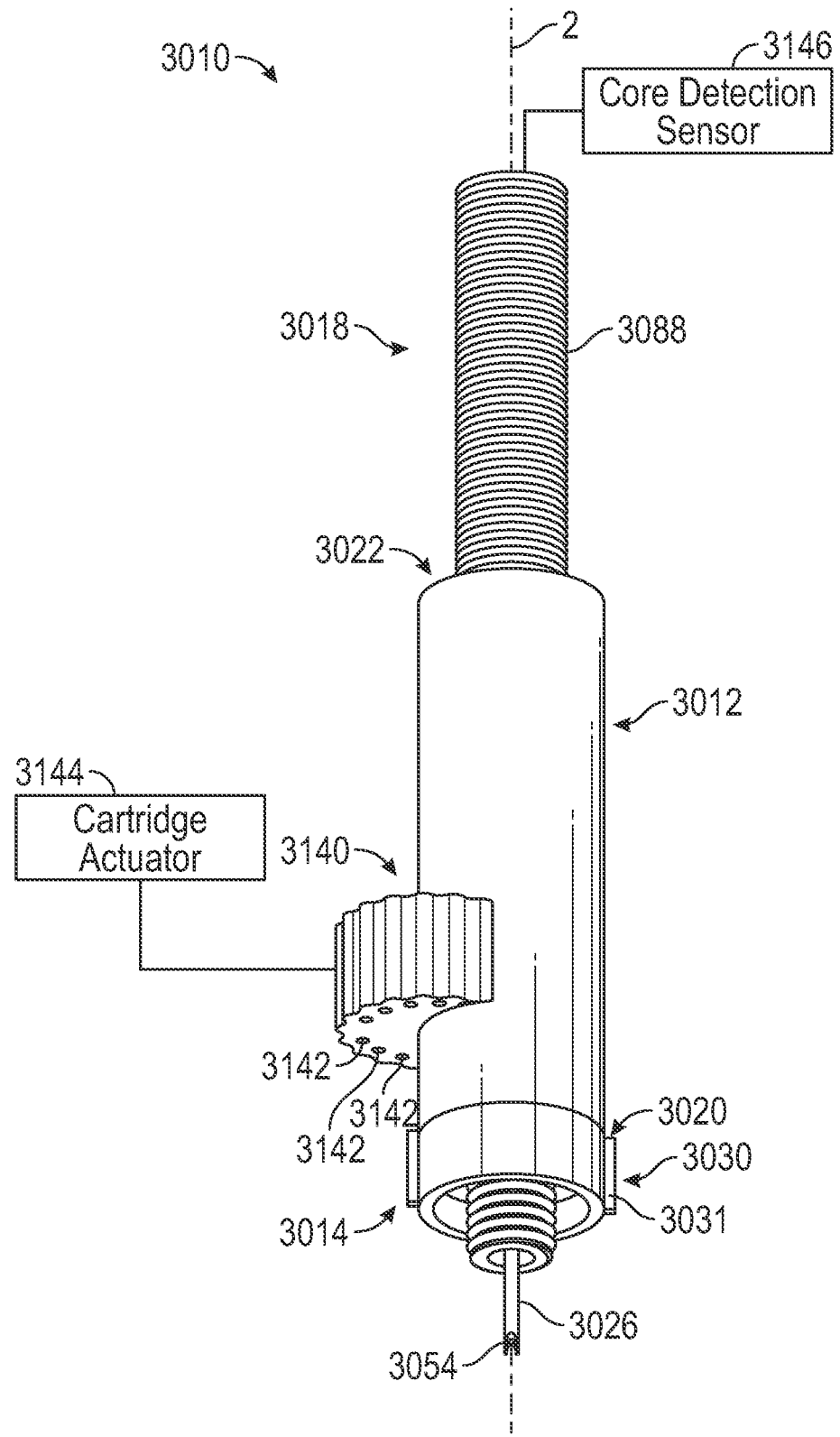
FIG. 20 is a perspective view of a hair transplant device including a revolving cartridge provided for storing a plurality of skin cores in accordance with one aspect of the present disclosure.

Referring now to FIG. 20, a hair transplant device 3010 including a skin core storage cartridge 3140 is illustrated. It is to be understood that like elements will be labeled using like reference numerals, with the exception that the numerals will be listed in the 3000's (e.g., hair transplant device 10 and hair transplant device 3010). Unless shown or described otherwise, it is to be understood that elements sharing like reference numerals are substantially similar to those previously described herein, including in their function. In the illustrated embodiment, the hair transplant device 3010 can be substantially similar to the hair transplant device 10 of FIGS. 1-16, with the exception that hair transplant device 3010 includes the cartridge 3140 coupled to a housing 3012. It is to be understood that, although not explicitly illustrated, an implanting unit, such as the implanting unit 16 of FIG. 1, could be coupled to the extraction unit 3014 of FIG. 20.

The cartridge 3140 can be configured to store a plurality of extracted skin cores, such that a plurality of hair follicle extractions could be conducted prior to a subsequent implant procedure. That is, as opposed to extracting/implanting a single skin core at a time, a plurality of skin cores could be extracted back to back prior to any implanting. The cartridge 3140 can be rotatably coupled to the housing 3012 between the proximal end 3020 and the distal end 3022. The cartridge 3140 is rotatable (e.g., resolvable) around an axis parallel to an axis defined by the coring needle 3026 (e.g. central axis 2). This axis of rotation is radially offset from the central axis 2. The cartridge 3140 can include a plurality of openings 3142. In the illustrated embodiment, the openings 3142 are configured as skin core storage chambers that extend axially through the cartridge 3140. Rotation of the cartridge 3140 can selectively align one of the plurality of openings 3142 into alignment with the coring lumen (not shown, see, e.g., coring lumen 42, FIG. 4).

During a hair transplant operation, the extraction unit 3014 can be used to extract a hair follicle from a donor site, as described above with respect to FIG. 12. After the extraction unit 3014 has cut a skin core 112 from a donor site 110, suction can be applied through the central lumen 94 of the pin 80 (see FIG. 4) to move the skin core containing a hair follicle up, through the coring needle 3026 and the coring lumen and into one of the plurality of storage chambers 3142 in axial alignment with the coring needle 3026, thereby loading a storage chamber 3142. Once the storage chamber 3142 has been loaded with the skin core, the rotating cartridge 3140 can be rotated to align the coring lumen with the next unloaded storage chamber 3142. This process can be repeated until a desired number (or every one) of the storage chambers 3142 of the cartridge 3140 has been loaded.

Once the desired number (or every one) of the storage chambers 3142 has been loaded, an implanting unit (not shown, see, e.g., implanting unit 16, FIG. 4) can be coupled to the extraction unit 3014 and then the implanting unit can create an opening in a recipient site 120, as described above with respect to FIG. 14. Then, the pin 80 (and/or positive pressure put into the central lumen 94) can move the skin core from a loaded storage chamber 3142, through the central lumen to the splitting needle 32 of the implanting unit 16, and into the small opening, thereby implanting the skin core within the recipient site 120, as described above with respect to FIGS. 14-16. This process can repeated several times until every skin core within the loaded cartridge 3140 has been implanted into the recipient site 120.

According to some embodiments, the selective rotation of the rotating cartridge 3140 can be done manually. According to the illustrated embodiment, the selective rotation of the cartridge 3140 by a cartridge actuator 3144 (e.g., a gear drive, an electric motor, etc.) coupled to the cartridge 3140. According to the illustrated embodiment, the hair transplant device 3010 can include a core detection sensor 3146 configured to detect a loaded/unloaded condition of a storage chamber 3142. The core detection sensor 3146 can be a light sensor, and IR sensor, or any other sensor configured for the detection of a loaded chamber. Rotation of the cartridge 3140 via the cartridge actuator 3144 and the loaded/unloaded condition sensing via the core detection sensor 3146 can be controlled using the automated system described above.

Figure 21:
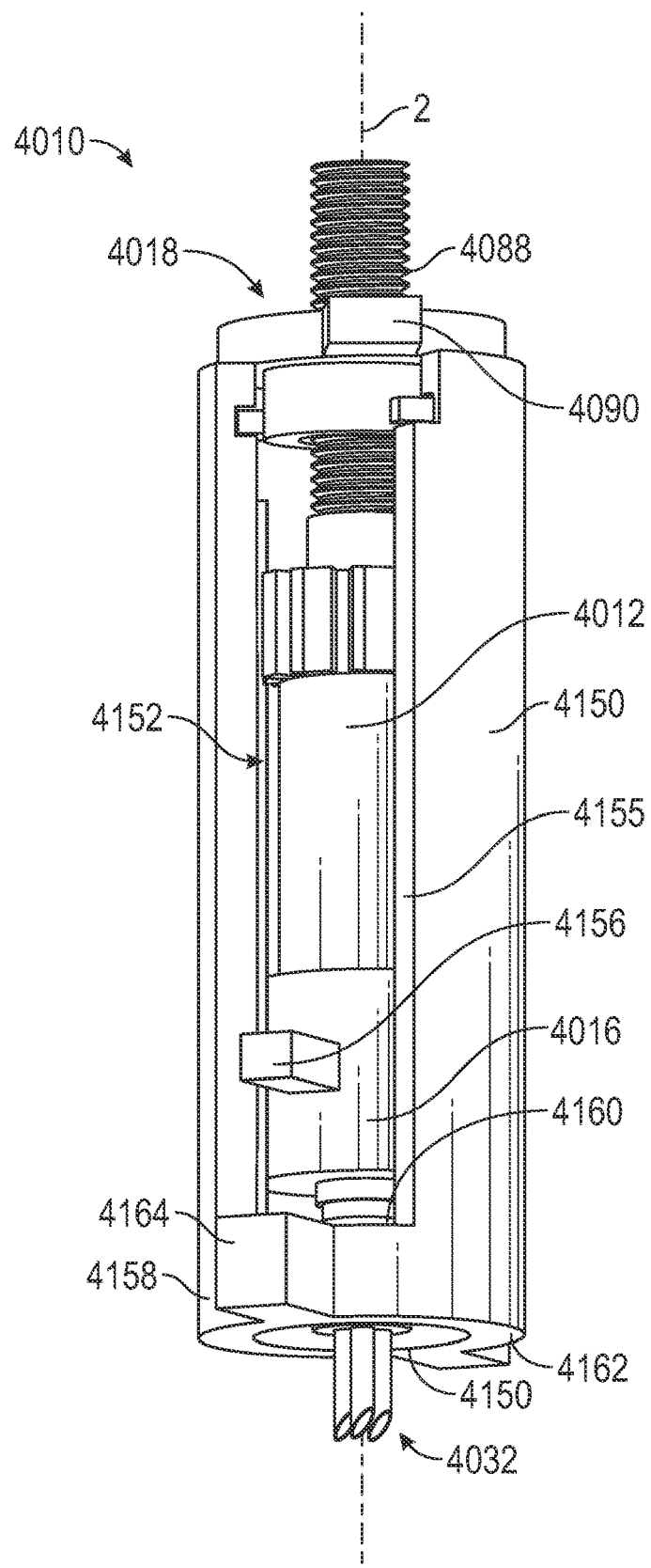
FIG. 21 is a perspective view of a hair transplant device including a casing in accordance with one aspect of the present disclosure.
Figure 22:
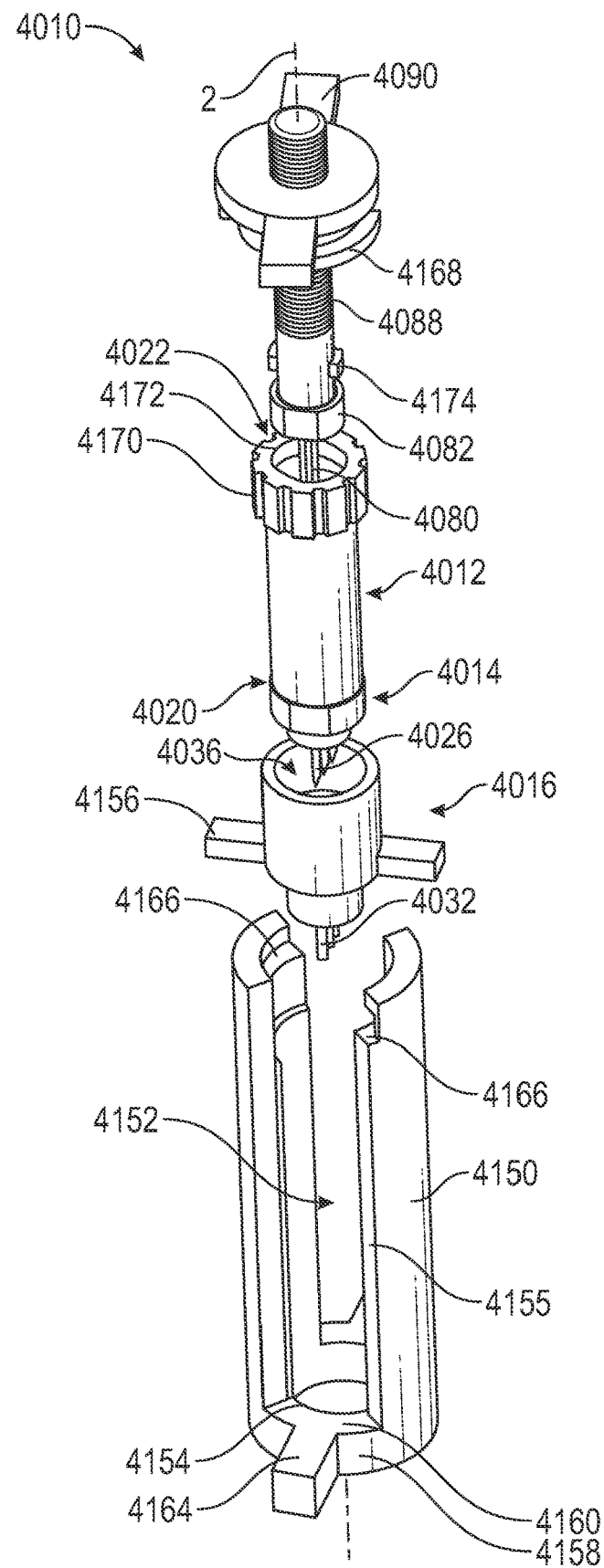
FIG. 22 is an exploded view of the hair transplant device of FIG. 21.

Referring now to FIGS. 21-22, a hair transplant device 4010 received within a casing 4150 is illustrated. It is to be understood that like elements will be labeled using like reference numerals, with the exception that the numerals will be listed in the 4000's (e.g., hair transplant device 10 and hair transplant device 4010). Unless shown or described otherwise, it is to be understood that elements sharing like reference numerals are substantially similar to those previously described herein, including in their function. In the illustrated embodiment, the hair transplant device 4010 can be substantially similar to the hair transplant device 1010 of FIGS. 17 and 18, with the exception that hair transplant device 4010 inserted into a casing 4150 that can add functionality to the hair transplant device 4010, and in some cases, improve the automation or ease of the extraction/implantation processes, as described below.

The casing 4150 is removably coupled to the hair transplant device 4010. With the hair transplant device 4010 inserted into the casing 4150, the casing 4150 can be configured to receive a portion of the user interface 4018 to lock an axial position of the pins 4080 (see FIG. 22). The casing 4150 can be configured to be held by an articulated arm or robotic arm, and can therefore be controlled by the automated system previously described. In the illustrated embodiment, the casing 4150 defines a substantially cylindrical shape with a hollow shaft 4152 (e.g., a cavity)

extending from a top side thereof towards the bottom side to receive the hair transplant device 4010.

The bottom side of the casing 4150 defines an opening 4154 to receive at least a portion of the implanting unit 4016 therethrough (e.g., the splitting needles 4032). The casing 4150 can also include one or more slots 4155 extending axially along the casing 4150 configured to provide access to the interior hollow shaft 4152 such that a user, or automated system, can interface with the hair transplant device. For example, the implanting unit 4016 can include protrusions 4156 extending radially outward from the implanting unit through the slot 4155 in the casing 4150. That way, a user can more readily interface with the implanting unit 4016 when the hair transplant device 4010 is assembled into the casing 4150.

The casing 4150 can also define a foot plate or flange 4158 at a bottom end of the casing 4150. An upper surface 4160 of the foot plate 4158 can define an axial stop for the hair transplant device 4010, for example, by providing a stop for the protrusions 4156 extending outwardly from the implanting unit 4016. A bottom surface 4162 of the casing 4150 can define an interface surface configured to contact a surface of the recipient site, as will be described. In the illustrated embodiment, the bottom surface 4162 is axially separated from the upper surface 4160. The casing 4150 can also include casing protrusions 4164 configured as a user interface or coupling with an automated system, such as an articulated arm. As will be described below, the casing 4150 can include a locking feature for locking an axial position of the pins 4080 relative to the housing 4012 (and also the casing 4150) via selective engagement with the user interface 4018.

Referring now to FIG. 22, an exploded view of the hair transplant device 4010 is illustrated. The casing 4150 can include a locking feature at the upper end of the casing 4150 configured as one or more radial slots 4166. In the illustrated embodiment, the radial slots 4166 extend radially outwards from, and circumferentially along an inner surface of the hollow shaft 4152.

Figure 23:
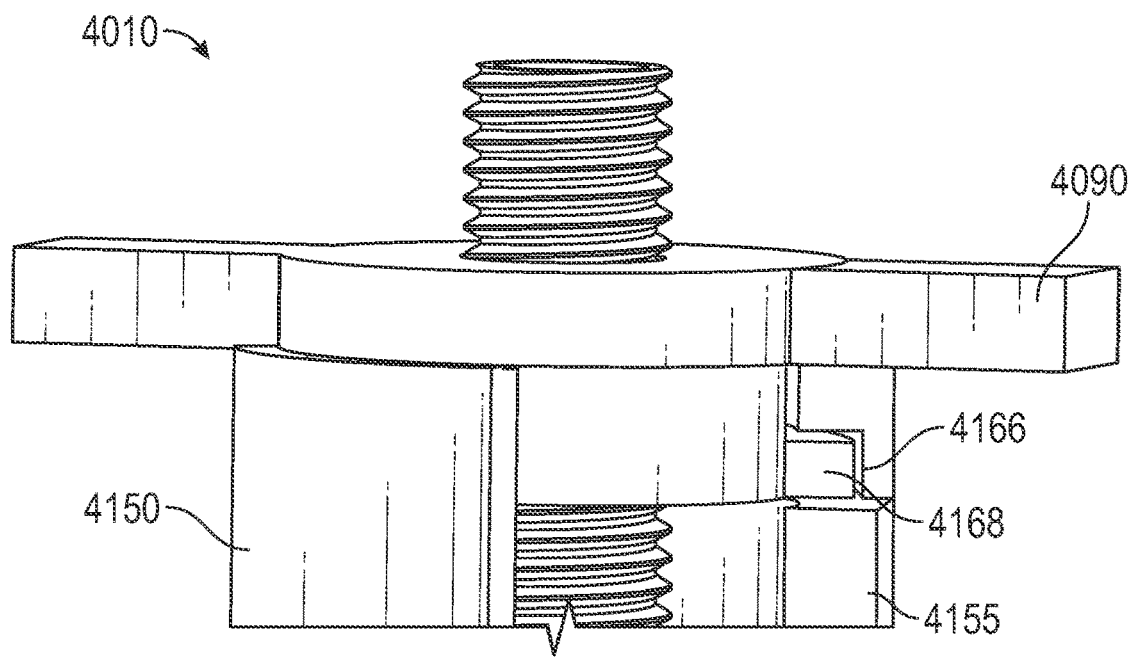
FIG. 23 is a close detail view of a user interface locking feature of the hair transplant device of FIG. 21.

As best illustrated in FIG. 23, when the hair transplant device 4010 is inserted into the casing 4150, the user interface 4018 can be axially advanced relative to the casing 4150 to a predetermined axial position. The user interface 4018 can include radial tabs 4168 extending radially outward therefrom. The radial tabs 4168 can be received within the slots 4155 and the user interface 4018 can be positioned such that the radial tabs 4168 are in alignment with the radial slots 4166 on the casing 4150. With the radial tabs 4168 of the user interface 4018 in alignment with the radial slots 4166 of the casing 4150, the user interface 4018 can then be rotated a predetermined amount (e.g., via the user interface flange 4090) to bring the radial tabs 4168 into engagement with the radial slots 4166, thereby locking an axial position of the user interface 4018 and the pins 4080 coupled thereto (see FIG. 22). In the illustrated embodiment, the engagement between the radial tabs 4168 in the user interface flange 4090 and the radial slots 4166 is the casing 4150 can be provided by an approximately 30 to 120 degree rotation of the user interface flange 4090. In the illustrated embodiment, the user interface flange includes two radial tabs 4168 that are circumferentially separated by about 180 degrees. Accordingly, the casing 4150 includes two circumferentially opposing radial slots 4166 to receive the radial tabs 4168.

Referring back to FIG. 22, the housing 4012 can include a locking feature adjacent to the distal end 4022 of the housing 4012 configured to provide an axial stop for the user interface 4018. In the illustrated embodiment, the locking feature is configured as a lock ring 4170. The lock ring 4170 can be rotatably coupled to the housing 4012. Alternatively, the lock ring 4170 can be integrally formed with the housing 4012. The lock ring 4170 defines a lock ring opening 4172 defining a profile that is configured to selectively provide an axial stop for the user interface 4018 (and the pins 4080 coupled thereto) upon selective rotation of the lock ring 4170. For example, the user interface body 4088 can include radial stops 4174 configured to engage the upper surface of the lock ring 4170 dependent upon the rotational position of one of the user interface 4018 or the lock ring 4170.

Figure 24:
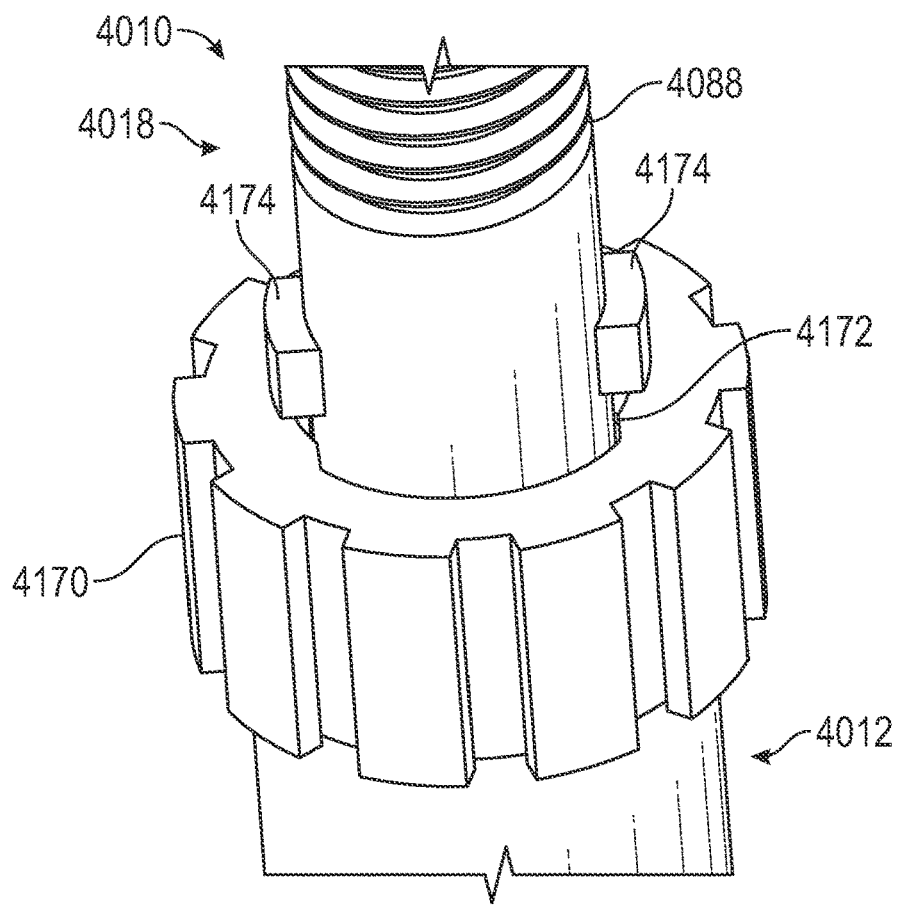
FIG. 24 is a close detail view of an axial stop feature of the hair transplant device of FIG. 21.

As best illustrated in FIG. 24, the user interface the user interface 4018 can be axially advanced relative to the casing 4150 to a predetermined axial position. The radial stops 4174 can engage the upper surface of the lock ring 4170, thereby providing an axial stop of the user interface 4018. The user interface 4018 can then be rotated relative to the lock ring 4170 (or vice versa) a predetermined amount to bring the radial stops 4174 into radial alignment with a portion of the profile of the opening 4172 configured to allow the radial stops 4174 to pass therethrough, then the user interface 4018, and the pins 4080 coupled thereto (see FIG. 22), can continue to be advanced past the axial stop. As such, the lock ring 4170 coupled to the housing 4012 can selectively provide an axial stop dependent upon a rotational position of the lock ring 4170 relative to the user interface 4018. In the illustrated embodiment, the engagement between the radial stops 4174 in the user interface body 4088 and the opening 4172 in the lock ring 4170 can be provided by an approximately 30 to 120 degree rotation of the user interface 4018 relative to the lock ring 4170. In the illustrated embodiment, the user interface body 408 includes two radial stops 4174 that are circumferentially separated by about 180 degrees. Accordingly, the opening 4172 in the lock ring 4170 defines a profile to receive the radial stops 4174 in a first rotational position, but provide a stop in a second rotational position.

Referring now to FIGS. 25-32, the hair transplant device 4010 can be used to perform a hair transplant operation on a patient, similar to the hair transplant operation of FIGS. 12-16. For example, the device 4010 is designed to perform an extraction procedure (shown in FIG. 25); a coupling procedure (shown in FIG. 26); an opening procedure (shown in FIG. 28); and an implantation procedure (shown in FIGS. 29-30). As such, only aspects that are otherwise different than those already explained above with respect to FIGS. 12-16 will be described below.

FIG. 25 illustrates the hair transplant device 4010 being used during an extraction procedure. As previously described, the coring needle 4026, in this case, a plurality of coring needles 4026 can be inserted into the donor site 110 forming a plurality of skin cores 112, with the distal cutting end of the coring needles 4026 cutting through the surrounding donor tissue 114. In the illustrated embodiment, the user interface 4018 is positioned such that the radial stops 4174 are in contact with the upper surface of the lock ring 4170, thereby holding the pins coupled to the user interface 4018 at a predetermined axial position (e.g., retracted). After insertion of the extraction unit 4014, the coring needles 4026 can then be removed from the donor site 110, still containing the skin cores 112 within the coring needles 4026, thereby leaving a plurality of small openings in the donor site 110. Next, as illustrated in FIG. 26, the implanting unit 4016 can be coupled to the extraction unit 4014 (e.g., via a coupling unit 70, see FIG. 7). Next, as illustrated in FIG. 27, the hair transplant device 4010 can be inserted into the hollow shaft 4152 of the casing 4150.

FIG. 28, illustrates the hair transplant device 4010 being used during an opening procedure. As illustrated, the hair transplant device 4010 can first be placed above a recipient site 120 of a recipient in an opening configuration. In the opening configuration, the user interface 4018 (and the pins, not shown) remains in the retracted position with the radial stops 4174 is engagement with the lock ring 4170. The splitting needles 4032, in this case a plurality of splitting needles 4032, can be inserted into the recipient site 120 until the lower surface of the foot plate 4158 engages the surface of the recipient site 120. The distal cutting edges forming a plurality of openings 124 in the tissue 122.

FIGS. 29-32 illustrate the hair transplant device 4010 being used during an implantation procedure. As illustrated in FIG. 28, with the distal cutting end of the splitting needles 4032 inserted into the small openings 124 created during the opening procedure, and the skin core 112 disposed within the coring needle 4026, the hair transplant device 4010 can be moved into the implantation configuration. In the implantation configuration, the splitting needles 4032 can remain in the small openings 124, and the lock ring 4170 can be rotated to allow the radial stops 4174 on the user interface 4018 to advance past the lock ring 4170, as shown in FIG. 29. Thus, the pins can be moved into the inserted position (e.g., via the user interface 4018). While the user interface 4018 is moved into the inserted position, the pins drive the skin cores 112 out of the coring needles 4026 and into the small openings 124. In the illustrated embodiment, the user interface can be advanced until either one of the protrusions 4156 on the implanting unit 4016 contact the upper surface of the foot plate 4158 or the user interface flange 4090 contacts the upper surface of the casing 4150.

After the skin core 112 has been pushed out of the coring needles 4026, into the small openings 124, the pins can be axially held in the inserted position by locking the user interface flange 4090, as illustrated in FIG. 30, by rotating the user interface 4018 relative to the casing 4150 to bring the radial tabs 4168 of the user interface flange 4090 into engagement with the radial slots 4166 of the casing 4150.

Figure 31:
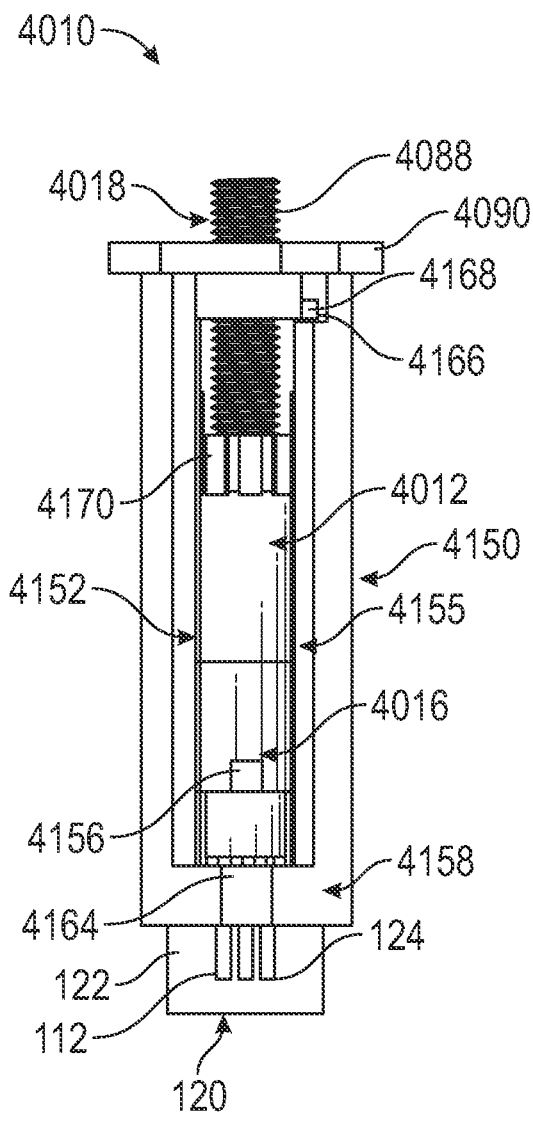
FIG. 31 is an illustration of a fourth step of hair follicle implanting utilizing the hair transplant device of FIG. 21.
Figure 32:
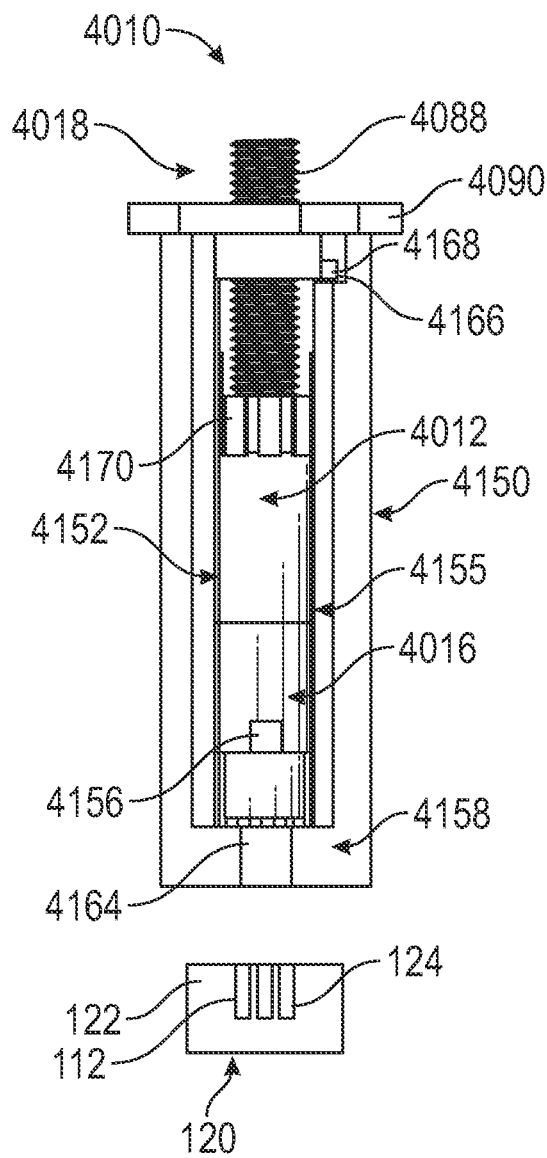
FIG. 32 is an illustration of a fifth step of hair follicle implanting utilizing the hair transplant device of FIG. 21.

The splitting needles 4032 of the implanting unit 4016 can then removed from the small openings 124 via movement of the implanting unit 4016 relative to the user interface 4018 with the user interface axially locked by the casing 4150, leaving the skin core 112 having the hair follicle implanted therein (FIG. 31). According to the illustrated procedure, the pins can then remain in contact with the skin cores 112 while the splitting needles 4032 are withdrawn from the recipient site 120. Next, the hair transplant device 4010 can be removed from the recipient site 120 (FIG. 32).

Referring now to FIGS. 33-36, a hair transplant device 5010 received within a casing 5150 have a cam sleeve 5180 is illustrated. It is to be understood that like elements will be labeled using like reference numerals, with the exception that the numerals will be listed in the 5000's (e.g., hair transplant device 10 and hair transplant device 5010). Unless shown or described otherwise, it is to be understood that elements sharing like reference numerals are substantially similar to those previously described herein, including in their function. In the illustrated embodiment, the hair transplant device 5010 can be substantially similar to the hair transplant device 4010 of FIG. 22, with the exception that the casing 5150 can include a cam sleeve 5180 that can add functionality to the hair transplant device 5010, and in some cases, improve the automation or ease of the extraction/implantation processes, as described below.

Figure 33:
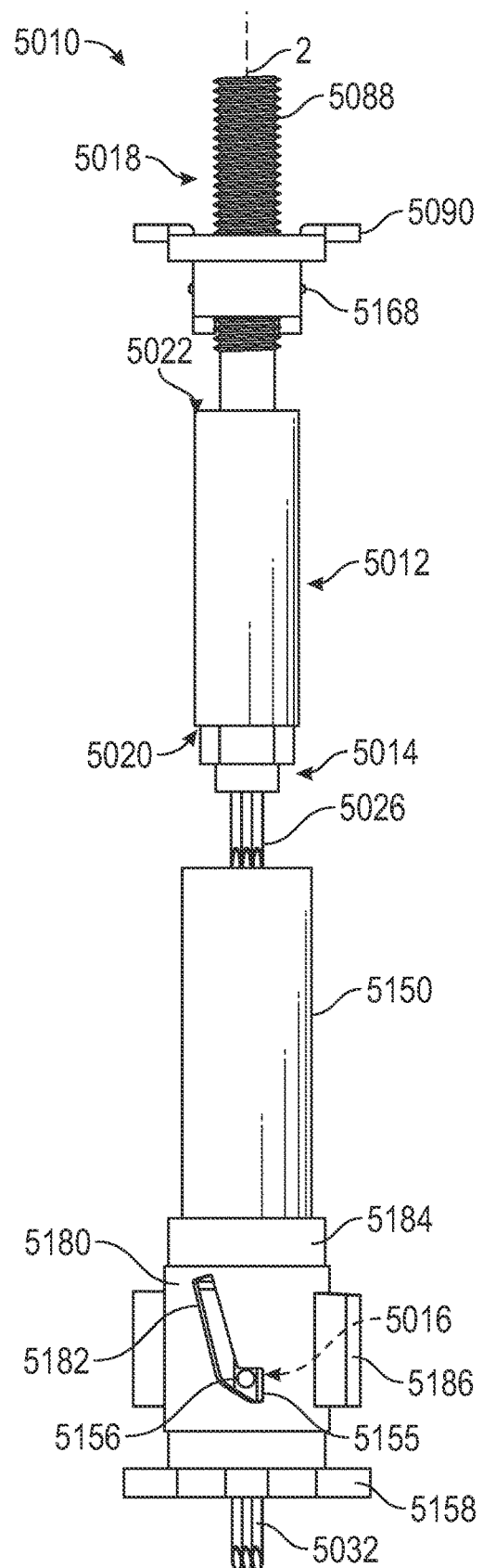
FIG. 33 is an exploded view of a hair transplant device including a casing with a cam sleeve in accordance with one aspect of the present disclosure.

With specific reference to FIG. 33, the hair transplant device 5010 can include a casing 5150 including a hollow shaft configured to receive the hair transplant device 5010. In the illustrated embodiment, the implanting unit 5016 can be pre-installed, or assembled with, the casing 5150. The casing 5150 can include a slot 5155 axially extending along a portion of the casing 5150 from an internal surface to an outer surface thereof. In the illustrated embodiment, the casing 5150 can include a cam sleeve 5180 arranged around the outer surface of the casing 5150 proximate the slots 5155 in the casing 5150. The cam sleeve 5180 can be configured to selectively extend (FIG. 34) or retract (FIG. 35) the implanting unit 5016 relative to the casing 5150, as will be described below. The cam sleeve 5180 can also include cam protrusions 5186 configured as a user interface or for coupling with an automated system.

Figure 35:
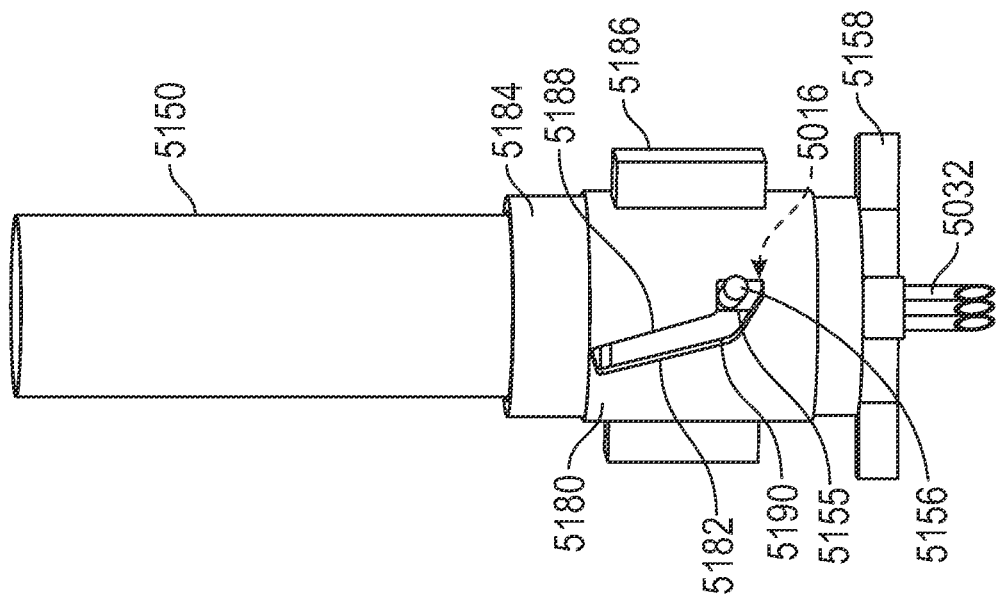
FIG. 35 is a side profile view of the hair transplant device of FIG. 33 with the implanting unit in an extended position.
Figure 34:
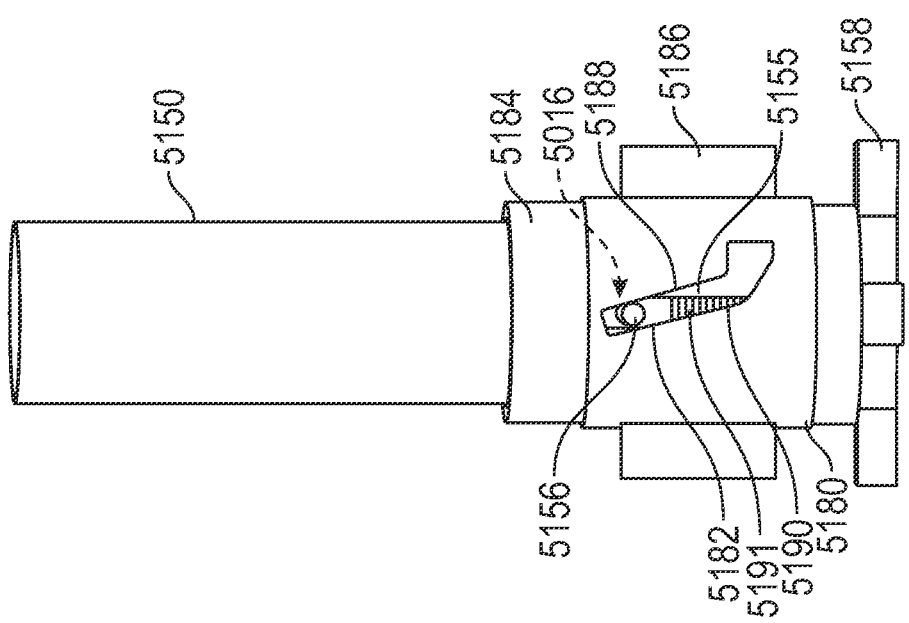
FIG. 34 is a side profile view of the hair transplant device of FIG. 33 with the implanting unit in a retracted position.

The cam sleeve 5180 can define a profiled slot 5182 configured to engage the protrusions 5156 extending radially outward from the implanting unit 5016 through the slot 5155 in the casing 5150. In the illustrated embodiment, a cam stop 5184 can prevent the cam sleeve 5180 from moving axially relative to the casing 5150. As best illustrated in FIG. 34, the implanting unit 5016 is arranged in the extracted position with the protrusion 5156 arranged at an upper end of the profiled slot 5182 of the cam sleeve 5180. To extend the implanting unit 5016 from the retracted position to the extended position, the cam sleeve 5180 can be rotated in a first direction (e.g., via the cam protrusions 5186), thereby bringing the implanting unit protrusion 5156 into engagement with a first ramped surface 5188 on the profiled slot 5182. The engagement between the implanting unit protrusions 5156 and the first ramped surface 5188 axially shifts the implanting unit 5016 relative to the casing 5150 and into the extended position (FIG. 35).

Similarly, to retract the implanting unit 5016 from the extended position to the retracted position, the cam sleeve 5180 can be rotated in a second direction (opposite the first direction), thereby bringing the implanting unit protrusion 5156 into engagement with a second ramped surface 5190 on the profiled slot 5182. The engagement between the implanting unit protrusions 5156 and the second ramped surface 5190 axially shifts the implanting unit 5016 relative to the casing 5150 and into the retracted position (FIG. 34). In the illustrated embodiment, a spring 5191 arranged between the casing 5150 and the implanting unit 5016 configured to bias the implanting unit in the retracted position. Additionally or alternatively, the implanting unit 5016 can be locked in the extended position and unlocked in the retracted position. For example, a ball lock, a detent lock, a snap-fit lock, a magnetic lock, or an electromagnetic lock can be arranged or included on the casing 5150 and be configured to lock the implanting unit 5016 in the extended position.

Figure 36:
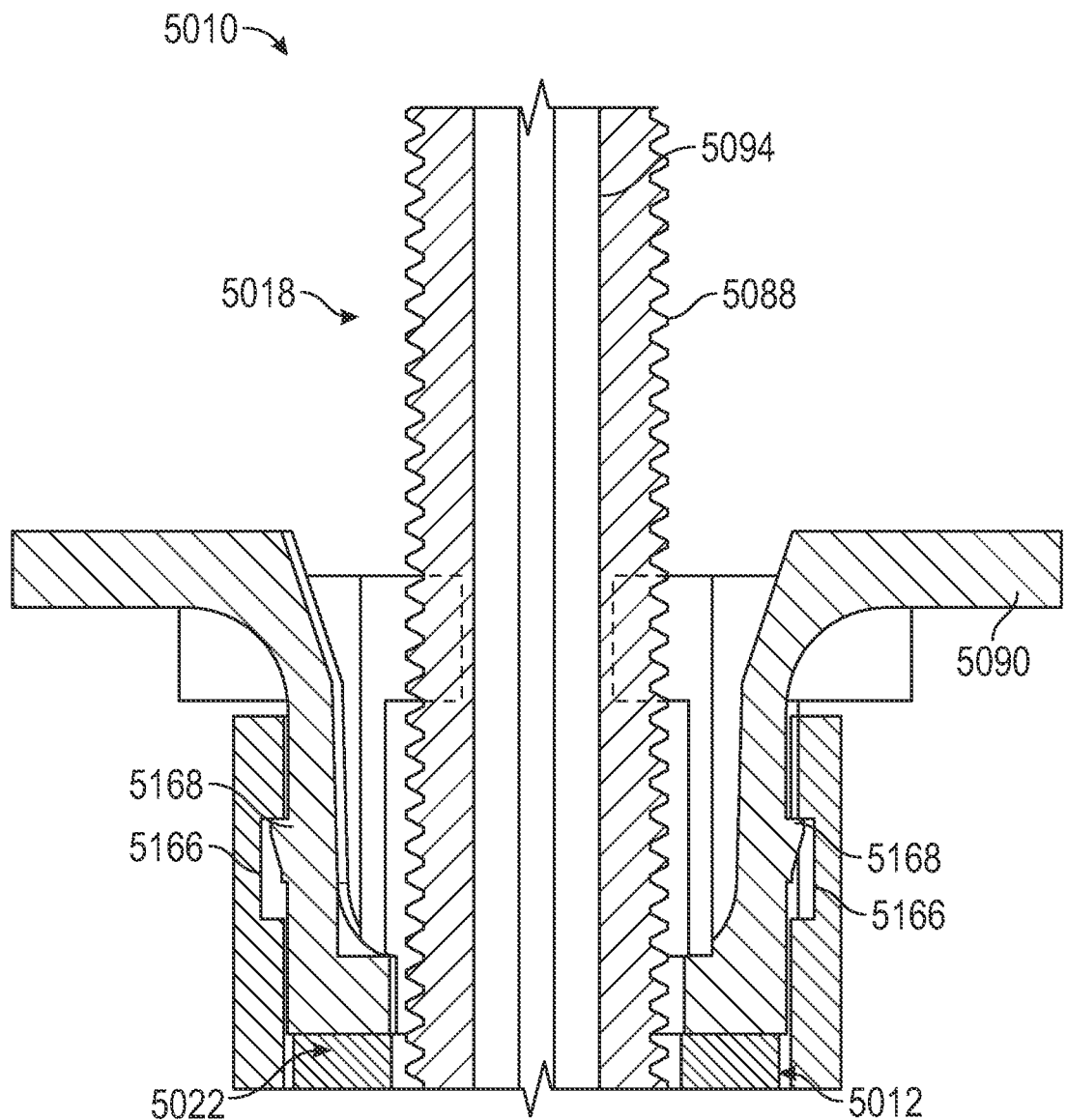
FIG. 36 is a close detail view of a user interface locking feature of the hair transplant device of FIG. 33

Referring now to FIG. 36, when the hair transplant device 5010 is inserted into the casing 5150, the user interface 5018 can be axially advanced relative to the casing 5150 to a predetermined axial position. The user interface 5018 can include radial tabs 5168 extending radially outward therefrom. As described below, the user interface flange 5090 and the radial tabs 5168 can be configured as a push-lock system to axially lock the user interface 5018 relative to the casing 5150 (and the housing 5012). The radial tabs 5168 can be received within the casing and the radial tabs 5168 can contact an inner surface of the casing 5150 to initially displace the tabs 5168 radially inward (e.g., elastically). The user interface 5018 can then be axially inserted into the predetermined position to bring the radial tabs 5168 into engagement with radial slots 5166 formed into the casing 5150. The radial tabs 5168 can then snap radially outward into the radial slots 5166, thereby locking an axial position of the user interface 5018 and the pins. To remove the user interface 5018 out of this axial position, the user interface flange 5090 can be squeeze or moved radially inward, bringing the radial tabs 5168 out of engagement with the radial slots 5166. The user interface 5018 may then again be freely moved axially. In the illustrated embodiment, the user interface flange 5090 includes two radial tabs 5168 that are circumferentially separated by about 180 degrees. Accordingly, the casing 5150 includes two circumferentially opposing radial slots 5166 to receive the radial tabs 5168. Additionally or alternatively, the user interface 5018 can be locked in the predetermined axial position. For example, a ball lock, a detent lock, a magnetic lock, or an electromagnetic lock can be arranged or included on the casing 5150 and be configured to lock the user interface 5018 in the predetermined axial position.

Referring now to FIGS. 37-38, the hair transplant device 5010 can be used to perform a hair transplant operation on a patient, similar to the hair transplant operation of FIGS. 12-16. For example, the device 5010 is designed to perform an extraction procedure; a coupling procedure; an opening procedure (shown in FIG. 37); and an implantation procedure (shown in FIGS. 37-39). As such, only aspects that are otherwise different than those already explained above with respect to FIGS. 12-16 will be described below. Specifically, in the illustrated procedure, the extraction procedure, the coupling procedure, and the opening procedure is not illustrated as it is done substantially the same as the extraction procedure, the coupling procedure, and the opening procedure described above with respect to FIGS. 12-14.

FIGS. 37-39 illustrate the hair transplant device 5010 being used during an implantation procedure. As illustrated in FIG. 28, with the distal cutting end of the splitting needles 5032 inserted into the small openings 124 created during the opening procedure, and the skin cores 112 disposed within the coring needles 5026 (see FIG. 33), the hair transplant device 5010 can be moved into the implantation configuration. In the implantation configuration, the splitting needles 5032 can remain in the small openings 124, the user interface 5018 can be advanced until the radial tabs 5168 lock with the casing 5150. Thus, the pins can be moved into the inserted position (e.g., via the user interface 5018). While the user interface 5018 is moved into the inserted position, the pins drive the skin cores 112 out of the coring needles 5026 and into the small openings 124.

After the skin core 112 has been pushed out of the coring needles 5026, into the small openings 124, the pins can be axially held in the inserted position by push-locking feature of the interface flange 5090, as previously described, to bring the radial tabs 5168 of the user interface flange 5090 into engagement with the radial slots 5166 of the casing 5150. The splitting needles 5032 of the implanting unit 5016 can then be removed from the small openings 124 via rotation of the cam sleeve 5180, as described above, leaving the skin core 112 having the hair follicle implanted therein (FIG. 38). According to the illustrated procedure, the pins can then remain in contact with the skin cores 112 while the splitting needles 5032 are withdrawn from the recipient site 120. Next, the pins can be withdrawn by unlocking the user interface 5018 from the casing 5150 and the hair transplant device 5010 can be removed from the recipient site 120 (FIG. 39).

Figure 41:
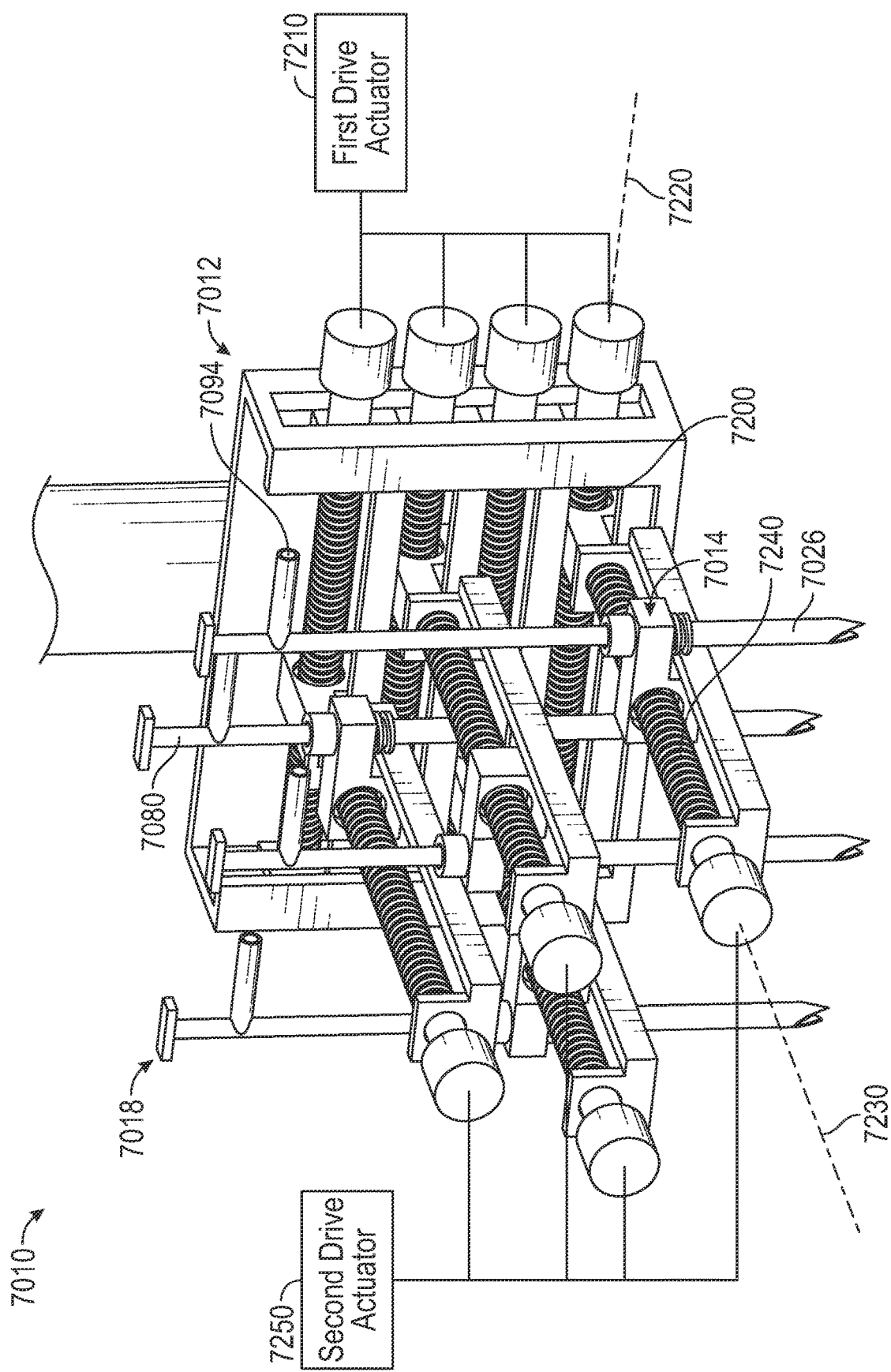
FIG. 41 is an illustration of hair transplant device including a non-linear array of coring needles.

Referring now to FIGS. 40 and 41, a hair transplant device 6010 for extracting tens, hundreds, or thousands of hair follicles simultaneously from a donor site of a donor and then implanting the tens, hundreds, or thousands of hair follicles simultaneously into a recipient site of a patient is illustrated. It is to be understood that like elements will be labeled using like reference numerals, with the exception that the numerals will be listed in the 6000's (e.g., hair transplant device 10 and hair transplant device 6010). Unless shown or described otherwise, it is to be understood that elements sharing like reference numerals are substantially similar to those previously described herein, including in their function. As can be seen in the illustration of FIG. 40, the hair transplant device 6010 includes a housing 6012 containing a plurality of extraction units 6014 with a corresponding plurality of pins 6080 movable relative to the coring needles 6026 of the extraction units 6014.

The coring needles 6026 can be independently movable relative to each other. Each coring needle 6026 needle can be moved in x, y, z, xy, yz, zx axes. So that the density of extracting the hair tissues can be varied. Similar to the devices previously described, splitting needles can be coupled end to end with the coring needles (e.g., via a coupling unit 70, see FIG. 7) and the implanting needles density can be varied. Thus, the hair tissues can be extracted at one density and implanted at a different density.

The hair transplant device 6010 includes an array of coring needles 6026, similar to the extraction unit 14 described above, and a user interface 6018 including an array of corresponding pins 6080, similar to the user interface 18 described above, may be used to extract a hair follicle (or multiple hair follicles). Again, the pins 6080 include a central lumen 6094 which can be coupled to a suction source or implanting agent source. An implant actuator 6092 can be coupled to the user interface 6018 such that the plurality of pins 6080 can either be actuated individually by a plurality of implant actuators, or actuated together by being coupled to a single implant actuator 6092.

As noted above, each coring needle 6026 needle can be moved in a plurality of axes. In the illustrated embodiment, each coring needle 6026 can be moved linearly along a single axis, independently, by being coupled to an axial drive system. In the illustrated embodiment, the axial drive system is a ball screw or linear rail 6200. The ball screws 6200 can be coupled to a drive actuator 6210 (e.g., an electric motor) or independently coupled to a plurality of drive actuators. The drive actuator 6210 can be configured to rotate the ball screws 6200 to adjust a position along a drive axis 6220. It should be noted the drive actuators can be configured to engage the automated system described above, for similar uses to those described above with reference to the hair transplant device 10.

The hair transplant device 6010 can also be configured for adjusting the vertical position (e.g., along the z-axis) of one or more of the plurality of coring needles 6026). For example, as illustrated in FIG. 40, a z-axis actuator 6212 can be coupled to the extraction unit 6014 such that the plurality of coring needles 6026 can either be actuated individually by a plurality of z-axis actuators, or actuated together by being coupled to a single z-axis actuator 6212. According to other embodiments, the ball screws 6200 can be arranged in different planes (e.g., through mechanical linkages), and the z-axis actuators can be coupled to the ball screws 6200 such that the z-axis actuators vertically position the ball screws 6200 themselves.

FIG. 41 illustrates a hair transplant device 7010 that includes a non-linear array of a plurality of coring needles 7026. It is to be understood that like elements will be labeled using like reference numerals, with the exception that the numerals will be listed in the 7000's (e.g., hair transplant device 6010 and hair transplant device 7010). Unless shown or described otherwise, it is to be understood that elements sharing like reference numerals are substantially similar to those previously described herein, including in their function. The hair transplant device 7010 of FIG. 41 is substantially similar to the hair transplant device 6010 of FIG. 40, with the exception that the coring needles 7026 are moveable about two drive axes.

Each coring needle 7026 needle can be moved in two axes, a first drive axis 7220 and a second drive axis 7230. In the illustrated embodiment, each coring needle 7026 can be moved linearly along the first drive axis 7220, independently, along first ball screws 7200 coupled to a first drive actuator 7210. Similarly, each coring needle 7026 can be moved linearly along the second drive axis 7230, independently, along second ball screws 7240 coupled to a second drive actuator 7250. As such, under control of the first and second drive actuators, the coring needles 7026 can be moved non-linearly along a plane, in order to control an extracting density at a donor site or, when coring needles 7026 are coupled to splitting needles, to control an implanting density at a recipient site. In the illustrated embodiment, the first drive axis 7220 is orthogonal to the second drive axis 7230. It is also to be understood that yet a third drive axis with a third drive actuator and a third ball screw can be incorporated to provide free movement of the coring needles along three axes.

While the invention may be susceptible to various modifications and alternative forms, specific embodiments have been shown by way of example in the drawings and have been described in detail herein. However, it should be understood that the invention is not intended to be limited to the particular forms disclosed. Thus, the invention is to cover all modifications, equivalents, and alternatives falling within the spirit and scope of the invention as defined by the following appended claims.

Figure 42:
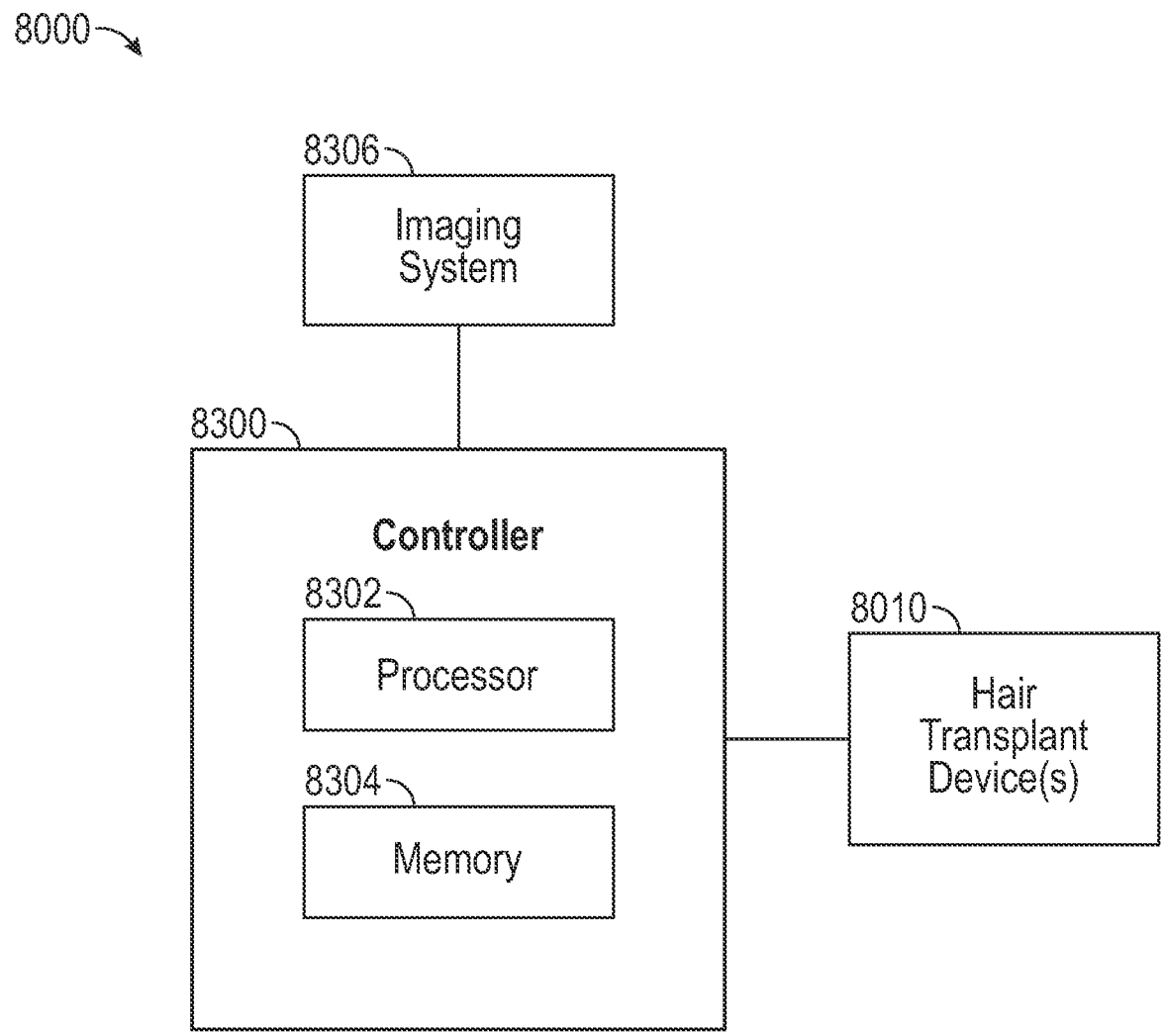
FIG. 42 is a schematic illustration of an automated hair transplant system in according with one aspect of the present disclosure.

For example, the hair transplant devices previously described can be incorporated into an automated hair transplant system, such as the transplant system described in U.S. patent application Ser. No. 16/629,657 entitled "Systems and Methods for Hair Transplant," the contents of which are incorporated herein by reference in its entirety. In general, as illustrated in FIG. 42, the hair transplant system 8000 may include a controller 8300 having one or more inputs, processors, memories, and outputs, and may be configured to operate a single hair transplant device 8010 and/or a matrix of hair transplant devices to carry out steps for extracting hair follicles from a donor site, creating an opening in a recipient site, and implanting the hair follicles in the recipient site. The hair transplant devices can include, for example, any of the hair transplant devices 10, 1010, 2010, 3010, 4010, 5010, 6010, or 7010 described above.

The hair transplant system 8000 may include, access, or communicate with one or more user interfaces and/or an imaging system 8306, by way of a wired or wireless connection to the inputs. In various implementations, the hair transplant system 8000 may include any computing device, apparatus or system configured for carrying out instructions and providing input/output capabilities, and may operate as part of, or in collaboration with other computing devices and sensors/detectors (local and remote). In this regard, the hair transplant system 8000 may be a system that is designed to integrate a variety of software and hardware capabilities and functionalities, and/or may be capable of operating autonomously.

The input may include any one or more different input elements, such as a mouse, keyboard, touchpad, touch screen, buttons, and the like, for receiving various selections and operational instructions from a user through touch, movement, speech, etc. The input may also include various drives and receptacles, such as flash-drives, USB drives, CD/DVD drives, and other computer-readable medium receptacles, for receiving various data and information. To this end, input may also include various communication ports and modules, such as Ethernet, Bluetooth, or Wi-Fi, for exchanging data and information with these, and other external computers, systems, devices, machines, mainframes, servers or networks.

In addition to being configured to carry out various steps for operating the hair transplant system, the processor 8302 may be configured to execute instructions, stored in the memory 8304 in a non-transitory computer-readable media. The instructions executable by the processor 8302 may correspond to various instruction for completing a hair transplant procedure (such as those previously described). Although the non-transitory computer-readable media can be included in the memory 8304, it may be appreciated that instructions executable by the processor 8302 may be additionally or alternatively stored in another data storage location having non-transitory computer-readable media.

In some aspects, the processor 8302 may be configured to receive and process image data from a subject, such as a donor or a recipient, captured by the imaging system 8306 to identify hair follicles and hair follicle orientations within a donor site of the donor and/or to determine implantation locations and necessary implantation angles within a recipient site of the recipient. In some aspects, the processor 8302 may access information and data, including video signals, stored in or emitted by the imaging system 8306. In some aspects, the imaging system 8306 may acquire either a single image or a continuous video signal using, for example, a camera, an infrared scanning system, or any other image capturing or video recording device that can be used to periodically image and/or scan and/or continuously record the subject.

In some instances, the imaging system 8306 may be may be utilized to align the coring needles of the hair transplant devices 8010 along a hair shaft or a plurality of hair shafts. In some non-limiting examples, the imaging system 8306 can include a camera such as a standard Cmos camera or an OCT imaging device. The OCT imaging device may allow for more precise alignment of the coring needles with reference to the hair shafts due to the capability of OCT imaging to see vertically into the tissue. Once the skin cores have been extracted, the hair transplant device 8010, under control of the automated hair transplant system 8000, may position itself over the recipient site for implantation of the hairs. A computer image may similarly be obtained of the recipient site that may show a natural hair line for the patient and direct where the hairs should be implanted. The ability of the needles to move independently may allow for better shaping and following of a natural hair line, such as in hair transplant devices 2010, 6010, or 7010. In some instances, the patient may be positioned in a support holder or laying down to limit movement during this process.

The output of the hair transplant system 8000 is configured to effectuate the operation of the hair transplant devices 8010. As such, the output may include various robotic devices capable of manipulating and operating the hair transplant devices 8010 and the interface features thereof, to effectuate extraction of hair follicles from a donor site, creation of openings within the recipient, and implantation of the hair follicles within the openings of the recipient, as described above, with reference to any of the hair transplant devices 10, 1010, 2010, 3010, 4010, 5010, 6010, or 7010.

As such, a user, such as a doctor or other hair transplant procedure personnel, can interact with a user interface of the hair transplant system 8000 to command the automated hair transplant system 8000 to effectuate a hair transplant procedure on a subject in accordance with any of the devices and methods described herein.

As such, the devices, systems, and methods described herein allow for a user to extract at least one hair follicle from a donor site, create at least one opening in a recipient site, and implant the at least one hair follicle in the at least one opening repetitively using a single device without the need for any physical manipulation of the at least one hair follicle. Accordingly, these devices, systems, and methods allow for more efficient, reliable, and predictable hair transplant procedures than compared to traditional devices, systems, and methods.

To apprise the public of the scope of this invention, the following claims are made.

We claim:

1. A hair transplant device comprising:
   an extraction unit including a coring needle configured to extract at least one hair follicle from a donor site;
   an implanting unit removably coupled to the extraction unit, the implanting unit including a splitting needle configured to create an opening in a recipient site;
   a housing coupled to the extraction unit; and
   a user interface extending from the housing and moveable relative to the housing;
   wherein when the extraction unit is assembled with the implanting unit, the coring needle and the splitting needle are arranged along a common axis and the coring needle and the splitting needle are axially separated such that the user interface can be displaced to drive the hair follicle from within the coring needle into the opening in the recipient site to implant the hair follicle.

2. The hair transplant device of claim 1, the coring needle having a first cutting end configured to cut into the donor site and a first coupling end opposite the first cutting end, the coring needle being coupled to the extraction unit at the first coupling end.

3. The hair transplant device of claim 2, the splitting needle having a second cutting end configured to cut into the recipient site and a second coupling end opposite the second cutting end.

4. The hair transplant device of claim 3, further comprising a coupling configured to connect the coring needle and the splitting needle together at the first cutting end and the second coupling end, respectively.

5. The hair transplant device of claim 4, wherein the coupling includes a hollow core such that a continuous lumen can be defined by the coring needle, the coupling, and the splitting needle.

6. The hair transplant device of claim 1, wherein the coring needle and the splitting needle define the same diameter.

7. The hair transplant device of claim 1, wherein the coring needle defines a first diameter and the splitting needle defines a second diameter, the first and second diameters being different.

8. The hair transplant device of claim 1, wherein the user interface includes a pin, the pin forming a central lumen in fluid communication with a coring lumen within the coring needle.

9. The hair transplant device of claim 8, wherein the central lumen is configured to deliver a gas or a liquid into the coring lumen of the coring needle while implanting the hair follicle into the recipient site.

10. The hair transplant device of claim 8, wherein the pin includes a mesh coupled to a distal end of the pin, the mesh configured to prevent the extracted hair follicle from entering into the central lumen of the pin.

11. The hair transplant device of claim 8, the central lumen being configured to be coupled to a suction source to deliver a suction force into the coring lumen of the coring needle to effectuate extracting the hair follicle from the donor site.

12. The hair transplant device of claim 8, the central lumen being configured to be coupled to a fluid source to deliver a liquid implanting agent into the coring lumen of the coring needle via the central lumen in the pin while implanting the hair follicle into the recipient site.

13. The hair transplant device of claim 12, wherein the liquid implanting agent comprises glycerol or polyethylene glycol.

14. The hair transplant device of claim 1, wherein the extraction unit further includes an extraction stop moveable relative to the coring needle and configured to adjust a coring depth, the extraction stop including a first interface surface that, during extraction of the hair follicle, is configured to contact a surface of the donor site at a predetermined coring depth.

15. The hair transplant device of claim 1, wherein the implanting unit further includes an implanting stop moveable relative to the splitting needle and configured to adjust an implanting depth, the implanting stop including a second interface surface that, during implanting of the hair follicle, is configured to contact a surface of the recipient site at a predetermined implanting depth.

16. The hair transplant device of claim 1, extraction unit includes guides configured to receive slots on the implanting unit to rotationally lock the implanting unit relative to the extraction unit.

17. The hair transplant device of claim 1, further comprising a casing at least partially surrounding the housing, the casing including a slot configured to receive at least a portion of the user interface to lock an axial position of the user interface relative to the housing.

18. The hair transplant device of claim 1, wherein the coring needle is a plurality of coring needles, each of the plurality of coring needles configured to extract one or more hair follicles from the donor site;
   the splitting needle is a plurality of splitting needles configured to create a corresponding plurality of openings in the recipient site; and
   a plurality of pins movable relative to the housing via the user interface, wherein each of the plurality of pins is configured to be received within one of the plurality of coring needles.

19. The hair transplant device of claim 18, wherein each of the plurality of coring needles or each of the plurality of splitting needles can be independently adjusted such that a density of extracting or implanting hair tissues can be varied.

20. The hair transplant device of claim 18, wherein an axial position of each of the plurality of coring needles is adjustable relative to the housing.

21. A hair transplant device comprising:
   an extraction unit configured to extract at least one hair follicle from a donor site, the extraction unit including a coring needle having a first cutting end configured to form a core from a donor site and a first coupling end opposite the first cutting end;

an implanting unit removably coupled to the extraction unit, the implanting unit including a splitting needle having a second cutting end configured to form an opening into a recipient site and a second coupling end opposite the second cutting end;

a housing coupled to the extraction unit;

a pin moveable relative to the housing and configured to be slidably received within the coring needle;

a coupling configured to connect the coring needle and the splitting needle together at the first cutting end and the second coupling end, respectively, when the extraction unit is assembled with the implanting unit;

a user interface coupled to the pin, wherein the user interface is configured to move a predetermined amount relative to the housing to control a depth of delivery of the hair follicle within the opening in the recipient site; and a casing removably coupled to the hair transplant device and at least partially surrounds the housing, the casing configured to receive the user interface to lock an axial position of the pin relative to the housing.

22. The hair transplant device of claim 21, wherein the casing defines a stop surface forming an axial stop for the implanting unit.

23. The hair transplant device of claim 22, wherein the casing further defines an interface surface configured to contact a surface of the recipient site, the interface surface being axially separated from the stop surface.

24. The hair transplant device of claim 21, further comprising a cartridge configured to rotate about a revolution axis that parallel to an axis defined by the coring needle, the cartridge including a plurality of openings to be selectively aligned with the coring needle such that cores from the donor site can be stored within each of the plurality of openings on the cartridge.

25. A method of performing a hair transplant procedure comprising:

driving a coring needle to engage a donor site to arrange a hair follicle within a coring lumen of the coring needle;

coupling a splitting needle to a cutting end of the coring needle with a coupling wherein the splitting needle and the coring needle are axially separated in the coupling;

driving the splitting needle to engage a recipient site to create an opening in the recipient site; and engaging a user interface to displace a pin axially aligned with the coring needle and the splitting needle to displace the hair follicle from within the coring lumen into the opening in the recipient site to implant the hair follicle.

26. The method of claim 25, wherein the pin forms a central lumen in fluid communication with the coring lumen.

27. The method of claim 26, further comprising applying suction to the coring lumen of the coring needle via the central lumen in the pin during or after the engagement of the coring needle with the donor site.

28. The method of claim 26, further comprising delivering an implanting agent into the coring lumen of the coring needle via the central lumen in the pin while implanting the hair follicle into the recipient site.

29. The method of claim 28, wherein the implanting agent comprises glycerol or polyethylene glycol.

* * * * *